(12) United States Patent
Greenwood et al.

(10) Patent No.: US 7,498,458 B2
(45) Date of Patent: Mar. 3, 2009

(54) PROCESS FOR THE PREPARATION OF PROSTAGLANDINS AND ANALOGUES THEREOF

(75) Inventors: Alan Kenneth Greenwood, Herts (GB); Derek McHattie, Herts (GB); David George Thompson, Gorsedd (GB); Derek Clissold, Berks (GB)

(73) Assignee: Resolution Chemicals Limited, Stevenage (GB)

( * ) Notice: Subject to any disclaimer, the term of this patent is extended or adjusted under 35 U.S.C. 154(b) by 21 days.

(21) Appl. No.: 11/189,985

(22) Filed: Jul. 27, 2005

(65) Prior Publication Data

US 2005/0261374 A1 Nov. 24, 2005

Related U.S. Application Data

(62) Division of application No. 10/478,513, filed as application No. PCT/GB02/02462 on May 24, 2002.

(30) Foreign Application Priority Data

May 24, 2001 (GB) .................................. 0112699.4

(51) Int. Cl.
 C07C 69/74 (2006.01)
(52) U.S. Cl. .................................................. 560/122
(58) Field of Classification Search ............... 549/263; 554/117, 175
 See application file for complete search history.

(56) References Cited

U.S. PATENT DOCUMENTS

| | | | |
|---|---|---|---|
| 3,549,688 A | 12/1970 | Finkbeiner et al. | |
| 3,778,450 A | 12/1973 | Axen | |
| 3,931,279 A | 1/1976 | Nelson | |
| 3,978,229 A | 8/1976 | Matsumoto et al. | |
| 4,036,832 A | 7/1977 | Hess et al. | |
| 4,088,775 A | 5/1978 | Skuballa et al. | |
| 4,158,667 A | 6/1979 | Axen | |
| 4,346,228 A | 8/1982 | Skuballa et al. | |
| 4,430,497 A | 2/1984 | Vollenberg et al. | |
| 4,680,415 A | 7/1987 | Holland et al. | |
| 5,223,537 A | 6/1993 | Stjernschantz et al. | |
| 5,321,128 A | 6/1994 | Stjernschantz et al. | |
| 6,184,250 B1 | 2/2001 | Klimko et al. | |
| 6,927,300 B2 | 8/2005 | Gutman et al. | |
| 7,268,239 B2 | 9/2007 | Greenwood et al. | |
| 2004/0249172 A1 | 12/2004 | Greenwood et al. | |

FOREIGN PATENT DOCUMENTS

| | | |
|---|---|---|
| DE | 43 23 331 A1 | 1/1995 |
| EP | 0 093 380 A2 | 11/1983 |
| EP | 0 305 180 A2 | 3/1989 |
| EP | 0 364 417 A1 | 4/1990 |
| EP | 0 305 180 A3 | 8/1990 |
| EP | 0 643 051 A1 | 3/1995 |
| EP | 0 472 338 | 8/1997 |
| GB | 1 366 215 | 9/1974 |
| GB | 1519861 | 8/1978 |
| GB | 1 449 147 | 9/1978 |
| JP | 50-18441 A | 2/1975 |
| JP | 50-18442 A | 2/1975 |
| JP | 51-131859 | 11/1976 |
| JP | 03-501025 A | 3/1991 |
| JP | 03-99074 A | 4/1991 |
| JP | 05-004982 A | 1/1993 |
| JP | 6-500804 A | 1/1994 |
| JP | 07-165703 | 6/1995 |
| JP | 10-182465 | 7/1998 |
| JP | 10-506893 A | 7/1998 |
| JP | 2003-531824 A | 10/2003 |
| WO | WO 89/01936 A1 | 3/1989 |
| WO | WO 90/02553 * | 3/1990 |
| WO | WO 92/02496 A1 | 2/1992 |
| WO | WO 93/00329 * | 1/1993 |
| WO | WO 93/00329 A1 | 1/1993 |
| WO | WO 94/07884 A1 | 4/1994 |
| WO | WO 95/07303 | 3/1995 |
| WO | WO 95/18102 A1 | 7/1995 |
| WO | WO 96/10407 A1 | 4/1996 |
| WO | WO 97/22602 A2 | 6/1997 |
| WO | WO 97/30710 A1 | 8/1997 |
| WO | WO 98/21181 | 5/1998 |
| WO | WO 99/02164 A1 | 1/1999 |
| WO | WO 99/02165 | 1/1999 |
| WO | WO 99/12899 A1 | 3/1999 |
| WO | WO 00/20386 A1 | 4/2000 |
| WO | WO 00/40246 A1 | 7/2000 |
| WO | WO 01/55101 A2 | 8/2001 |
| WO | WO 01/57015 A1 | 8/2001 |
| WO | WO 01/67816 A1 | 11/2001 |

OTHER PUBLICATIONS

Liljebris et al., Tetrahedron, 1995, 51(33), 9139-9154.*
Bundy, G.L., et al., "Synthesis and biological activity of prostaglandin lactones," *J. Med. Chem* 26:1089-1099, American Chemical Society (1983).
Corey, E.J., and Venkateswarlu, A., "Protection of Hydroxyl Groups as tert-Butyldimethylsilyl Derivatives," *J. Am. Chem. Soc.* 94:6190-6191, American Chemical Society (1972).
Database CAPLUS, Accession No. 2000:475544, Document No. 133:94548, Abstract for Stjernschantz, J., and Bahram, R., "Method and composition for treatment of female sexual dysfunction," PCT Intl. Appl. WO 2004040248 (May 2004).
Database CAPLUS, Accession No. 2002:978473, Document No. 138:39141, Burk, R.M., "Preparation of cyclopentance heptan(ene)oic acid, 2-heteroarylalkenyl derivatives as ocular hypotensives," United States Patent 6,310,087 (Oct. 30, 2001).

(Continued)

*Primary Examiner*—Zinna N Davis
(74) *Attorney, Agent, or Firm*—Sterne, Kessler, Goldstein & Fox P.L.L.C.

(57) ABSTRACT

Disclosed are processes for the synthesis and purification of prostaglandins and analogues thereof, especially analogues of $PGF_{2\alpha}$.

22 Claims, No Drawings

OTHER PUBLICATIONS de Nooy, A.E.J., et al., "On the Use of Stable Organic Nitroxyl Radicals for the Oxidation of Primary and Secondary Alcohols," *Synthesis* pp. 1153-1174, Thieme (1996).

Greene, T.W., "Protection for the Hydroxyl Group Including 1,2- and 1,3-Diols," in *Protective Groups in Organic Synthesis*, pp. 10-11 and pp. 39-41, 179, John Wiley & Sons, Inc., (1981).

Kawada, K., et al., "Prostglandin Photoaffinity Probes: Synthesis and Biological Activity of Azide-Substituted 16-Phenoxy- and 17-Phenyl-PGF$_{2\alpha}$ Prostaglandins," *J. Med. Chem.* 32:256-264, American Chemical Society (1989).

Lai, S., et al., "Enantioselective Synthesis of 12-*epi*-PGF$_{2\alpha}$ and 12,15-*diepi*-PGF$_{2\alpha}$," *J. Org. Chem.* 64:7213-7217, American Chemical Society (1999).

Mai, J., et al., "Prostaglandins and Thromboxane: *tert*-Butyldimethylsilyl Ethers as Derivatives for Their Analyses by Gas Chromatography-Mass Spectrometry-Selected Ion Monitoring," *J. Chromatography* 254:91-107, Elsevier Scientific Publishing Company (1983).

Resul, B., et al., "Phenyl-Substituted Prostaglandins: Potent and Selective Antiglaucoma Agnets," *J. Med. Chem.* 36:243-248, American Chemical Society (1993).

Skuballa, W., et al., "15,15-Ketals of Natural Prostaglandins and Prostaglandin Analogues. Synthesis and Biological Activities," *J. Med. Chem.* 21:443-447, American Chemical Society (1978).

Szederkenyi, F., et al., "Selective trimethylsilylation for the determination of 16(S)-amino-PGF$_{2\alpha}$ methyl ester by gas-liquid chromatography," *J. Chromatography* 333:404-411, Elsevier Science Publishers B.V. (1985).

Ogawa, Y., et al., "A Novel Synthesis of Prostaglandin D$_2$," *J. Org. Chem.* 51:1625-1627, American Chemical Society (1986).

Notice of Allowance mailed on Apr. 26, 2007 in U.S. Appl. No. 11/189,986, Greenwood, A.K., et al., filed Jul. 27, 2005.

Office Action mailed on Dec. 20, 2006 in U.S. Appl. No. 11/189,986, Greenwood, A.K., et al., filed Jul. 27, 2005.

Office Action mailed on Apr. 10, 2006 in U.S. Appl. No. 11/189,986, Greenwood, A.K., et al., filed Jul. 27, 2005.

Office Action mailed on Jan. 9, 2008 in U.S. Appl. No. 10/478,513, Greenwood, A.K., et al., § 371, filed Jun. 8, 2004.

Office Action mailed on Jul. 18, 2007, U.S. Appl. No. 10/478,513, Greenwood, A.K., et al., § 371 filed June 8, 2004.

Office Action mailed on Jul. 18, 2006 in U.S. Appl. No. 10/478,513, Greenwood, A.K., et al., § filed Jun. 8, 2004.

Database CAPLUS, Accession No. 1979:592566, Document No. 91:192868, Abstract for Morozowich, W., et al., "Prostaglandin prodrugs, II: New method for synthesizing prostalandin C1-allphatic astars," *J. Pharm. Sci.* 68:836-638 (1979). American Chemical Society(1979).

Database CAPLUS, Accession No. 1982-155862, Document No. 98-155682. Abstract for Miyazam. H., et al., "Dimathylisopropylsllyl ether derivatives in gas chromatography mass spectrometry of prostagiandin and thromboxane B2," *Biomed. Mass. Spectrom.* 8:521-526 (1981), American Chemcial Society (1982).

Database CAPLUS, Accession No. 1983:467497, Document No. 99:87497, Abstract for Waddell, K.A., et al., "Combined capillary column gas chromatography negative ion chemical inization mass spectrometry at promanoids." *Biomed. Mass Spectrom.* 10:83-88 (1983), American Chemical Society (1983).

Database CAPLUS, Accession No. 1986:533646, Document No. 105:133846, Abstract for Ikagami, S., et al., Japanese Patent Publication No. JP 61-60690 A2 (1986), American Chemical Society (1986).

Database CAPLUS, Accession No. 1988:492547, Document No. 109-92547, Diycamo, I., et al., "Derivatization of prostaglandin and related compounds to (methozime) alkyl ester alkyl ether derivatives for gas chromatographic analysis," *J. Chromatogr.* 435:219-226 (1986), American Chemical Society (1988).

Liljebris, C., et al., "Ligand-Controlled Pailadiums-Catalyzed Intramolecular Reactions of Phenyl-Substituted Prostaglandin F$_2$ Analogues," *Tetrahedron* 51:9139-9154, Elsevier Science (1995).

Miftakhov, M.S., et al., "Prostanoids. XXXII. Synthesis of (+)-prostaglandin F2α," *Z. Org. Khim.* 26:1476-1484, Nauka (1990).

Database CAPLUS, Accession No. 1991:81308, Document No. 114:81308, English language abstract for Miftakhov, M.S. et al., "Prostanoids. XXXII. Synthesis of (+)-prostaglandin F2α," *Z. Org. Khim.* 26:1476-1484 (1990). American Chemical Society (1991).

Dialog File 351, Accession No. 10143337, Derwent WPI English language abstract for German Patent Publication DE 43 23 331 A1, Derwent Information Ltd. (1995).

Dialog File 351, Accession No. 679656, English language abstract for JP 50-18441 A (attached on PTO/SB/08A as document FP4), 2008.

Dialog File 351, Accession No. 679655, English language abstract for JP 50-18442 A (attached on PTO/SB/08A as document FP5), 2008.

Liljebris, C., et al., "Derivatives of 17-Phenyl-18, 19, 20-trinorprostaglandin F$_{2a}$ Isopropyl Ester: Potential Antiglaucoma Agents, " *J. Med. Chem.* 38:289-304, American Chemical Society (1995).

Miftakhov, M.S., et al., Synthesis of (+)-Prostaglandin F$_{2a}$ *J. Org. Chem. USSR.* 26:1274-1280, Plenum Publishing Corporation (1990).

Schaaf, T.K., et al "N-(Methanesulfonyl)-16-phenoxyprostaglandincarboxamides: Tissue-Selective, Uterine Stimulants, " *J. Med. Chem.* 24:1353-1359, American Chemical Society (1981).

Theil, F., et al., "Synthesis of a Stable Prostacyclin Analogue, " *J. Prakt. Chem.* 330:766-774, Wiley-VCH (1988).

Tolstikov, G.A., et al., "Selective Oxidatiion of 7α Hydroxy-6β-Hydroxymethylene-2-Oxabicyclo[3.3.0]Octan-3-One Bistrimethylsilyl Ether by Reagents Based on Chromium(VI) as Key Stage in Synthesis of Sulprostone, " *J. Org. Chem. USSR.* 25:1908-1941, Plenum Publishing Corporation (1990).

Dialog File 351, Accession No. 5390939, English language abstract for JP 03-501025 A (attached on PTO/SB/08A as document FP13), no date provided.

Dialog File 351, Accession No. 5561546, English language abstract for JP 03-99074 A (attached on PTO/SB/08A as document FP14), no date provided.

Dialog File 351, Accession No. 5840790, English language abstract for JP 05-004982 A (attached on PTO/SB/08A as document FP15), no date provided.

Dialog File 351, Accession No. 7354662, English language abstract for JP 07-165703 A (attached on PTO/SB/08A as document FP16), no date provided.

Dialog File 351, Accession No. 7354662, English language abstract for JP 10-182465 A (attached of PTO/SB/08 A as document FP17), no date provided.

\* cited by examiner

PROCESS FOR THE PREPARATION OF PROSTAGLANDINS AND ANALOGUES THEREOF

CROSS REFERENCE TO RELATED APPLICATIONS

This application is a divisional of U.S. application Ser. No. 10/478,513, having a 35 U.S.C. §371 date of Jun. 8, 2004. U.S. application Ser. No. 10/478,513 is a National Phase filing under 35 U.S.C. §371 of International Application No. PCT/GB02/02462, filed May 24, 2002. International Application No. PCT/GB02/02462 claims priority to GB 0112699.4, filed May 24, 2001. All of the above mentioned applications are hereby incorporated by reference in their entirety.

The present invention relates to a novel process for the synthesis of prostaglandins and prostaglandin analogues. In particular, this invention relates to the synthesis of $PGF_{2\alpha}$ and analogues thereof.

Prostaglandin $F_{2\alpha}$ {$PGF_{2\alpha}$-7-[3,5-dihydroxy-2-(3-hydroxy-1-octenyl)-cyclo-pentyl]-5-heptenoic acid]} has the structure:

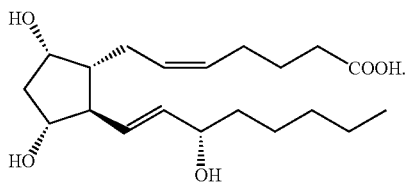

This compound causes uterine contraction and is used clinically to induce and accelerate labour, and as an abortifacient.

Prostaglandins are generally characterised by the substituents on the cyclopentyl ring. The $PGF_{2\alpha}$ prostaglandins and prostaglandin analogues generally have two hydroxyl groups in a cis configuration relative to the cyclopentane ring, and two side chains in a trans configuration relative to each other, each side chain having one double bond. Analogues of $PGF_{2\alpha}$ can have a different number of double bonds in the side chains, and the substituents along the side chains may vary. Additionally, in some $PGF_{2\alpha}$ analogues, the side chain carboxylic acid group may be esterified.

Examples of $PGF_{2\alpha}$ analogues having therapeutic use are cloprostenol, which contains a chlorophenyl ether side chain substituent, fluprostenol, which contains a trifluoromethylphenyl ether side chain substituent, and travoprost:

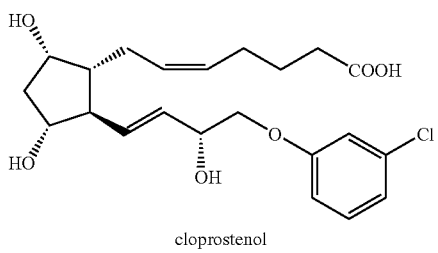

cloprostenol

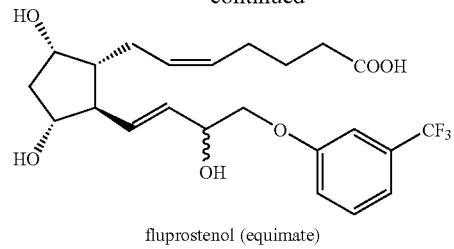

fluprostenol (equimate)

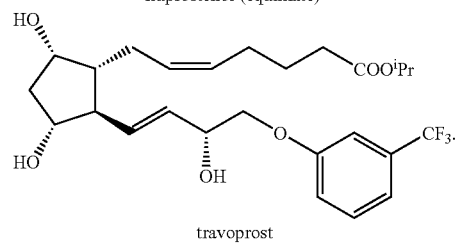

travoprost

These compounds have prostaglandin F agonist activity and are used in the clinic for treating glaucoma and ocular hypertension.

Latanoprost [13,14-dihydro-15(R)-17-phenyl-18,19,20-trinor-$PGF_{2\alpha}$-isopropyl] is an example of a $PGF_{2\alpha}$ analogue having one saturated side chain and wherein the carboxylic acid group is esterified:

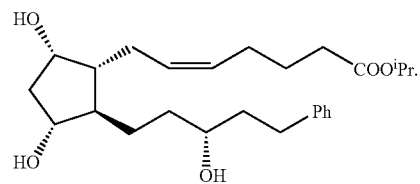

This compound is used in the clinic for the reduction of elevated intra-ocular pressure in patients with open angle glaucoma and ocular hypertension.

Prostaglandin analogues based on $PGF_{2\alpha}$ for use in the treatment of glaucoma and ocular hypertension are described in, for example, European patent number 0 364 417 B1. The procedures for the synthesis of $PGF_{2\alpha}$ analogues described therein start from an advanced-stage intermediate, 16-phenyl-17,18,19,20-trinor $PGF_{2\alpha}$, or the tetranor homologue thereof.

European patent number EP 0 544 899 B1 describes a process for the synthesis of 13,14-dihydro-15(R)-17-phenyl-18,19,20-trinor-$PGF_{2\alpha}$ esters of the formula:

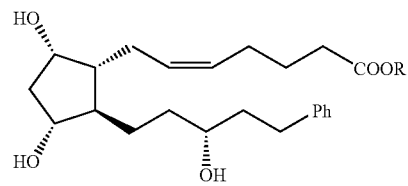

wherein the group R represents alkyl, phenyl or benzyl. The starting material for the process disclosed therein is the para-phenylbenzoyl (PPB)-protected Corey lactone:

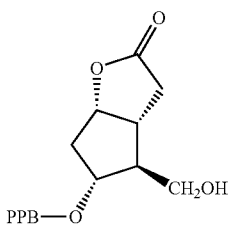

In the disclosed process, the intermediate of formula:

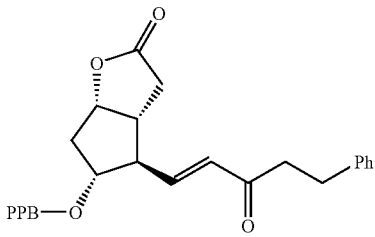

is prepared by transforming the hydroxymethyl group of the protected Corey lactone, with an oxidising agent (dicyclohexylcarbodiimide) to form the corresponding aldehyde. Reaction of the aldehyde with a phenylphosphonium salt forms the above intermediate.

The intermediate is then reduced to form the corresponding hydroxy compound, which is subjected to a hydrogenation reaction to form the saturated side chain intermediate of the formula:

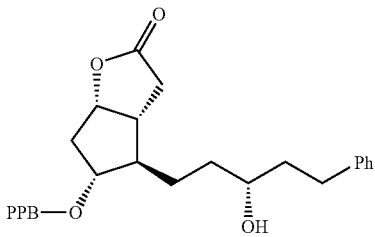

The lactone oxo group of the above intermediate is reduced to form the corresponding hydroxy analogue, which is subsequently deprotected to give the following intermediate:

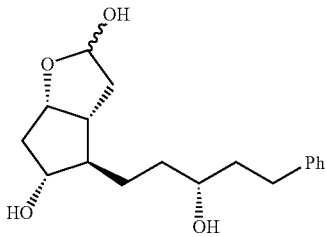

A subsequent Wittig reaction followed by esterification forms the desired $PGF_{2\alpha}$ product.

The process disclosed in EP 0 544 899 B1 suffers from a major drawback in that only moderate or low yields are achieved in certain steps. In particular, according to the examples, the yield for the first step (reaction of the PPB-protected Corey lactone with triphenyl-(4-phenyl-3-oxobutyl-phosphonium iodide on a small scale was only around 49%. Even on a large scale, the reported yield was only around 53%.

These low yields at the outset result in, at best, difficulties in purifying the intermediates, and at worse, a loss of valuable and expensive starting material. Additionally, the reported yield of 38% in the second step (reduction of the side chain oxo group), is also less than satisfactory.

Furthermore, only moderate yields are achieved in subsequent reaction steps, resulting in a dramatic reduction of the overall yield.

In an alternative synthesis described in B. Resul et al, J. Med. Chem. (1993), 36, pp. 243-248, a similar route was employed, with the exception that the deprotection step was carried out before the reduction of the oxo group of the lactone. This process also suffers from low yields (about 58%) in the first step, and only moderate or low yields were reported for subsequent steps.

In view of the prior art procedures and the problems associated therewith, it is an object of the present invention to provide an alternative process for the synthesis of $PGF_{2\alpha}$ and analogues and salts thereof. Further objects of at least specific embodiments of the invention include the provision of a synthetic route with good yields and intermediates that can be readily purified.

Accordingly, the present invention provides a process for the preparation of prostaglandin derivatives having the Formulae (I-A) and (I-B):

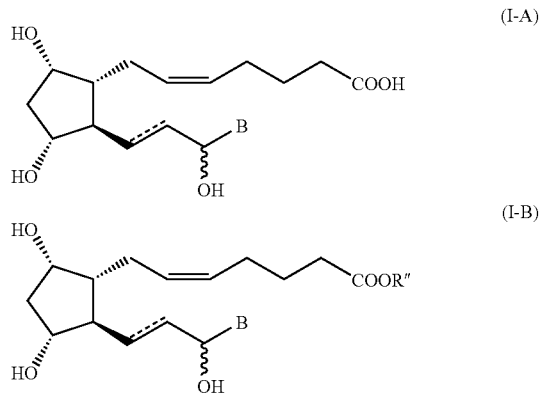

wherein:

B represents a substituent selected from the group consisting of:

(i) $C_1$ to $C_8$ alkyl, (ii) $C_7$ to $C_{16}$ aralkyl, wherein the aryl group may be unsubstituted or substituted with one to three substituents independently selected from the group consisting of $C_1$ to $C_6$ alkyl, halo and $CF_3$; and (iii) —$(CH_2)_nOR^a$, wherein n represents 1, 2 or 3 and $R^a$ represents a $C_6$ to $C_{10}$ aryl group which may be unsubstituted or substituted with one to three substituents independently selected from the group consisting of $C_1$ to $C_6$ alkyl, halo or $CF_3$; and R" represents $C_1$-$C_{20}$ alkyl (preferably a $C_1$ to $C_6$ alkyl group, e.g. methyl, ethyl, propyl and isopropyl), $C_3$ to $C_8$ cycloalkyl (e.g. cyclohexyl, cyclopropyl, cyclobutyl) or $C_6$ to $C_{10}$ aryl (preferably phenyl). A preferred R" group is isopropyl.

It will be appreciated by a person of skill in the art that the present invention can be applied to the synthesis of compounds of Formula (I-A) and (I-B) wherein R" is other than an alkyl, cycloalkyl or aryl group. In fact, the group R" can represent any group that can be introduced by reaction of an acid intermediate of the compound of Formula (I-A) or (I-B) with a compound R"-X (X=halo, and preferably iodo) In the presence of a base, such as DBU. Examples of other suitable R" groups include, but are not limited to, unsaturated $C_1$ to $C_{20}$ alkyl, unsaturated $C_3$ to $C_8$ cycloalkyl, wherein the saturated or unsaturated alkyl or cycloalkyl groups, or aryl groups can be substituted with one or more (typically 1 to 3) substituents such as $CF_3$, $C_1$ to $C_6$ alkoxy, CN. Other examples of suitable R" groups include $C_6$ to $C_{10}$ heterocycloalkyl (e.g. piperidinyl), $C_6$ to $C_{10}$ heteroaryl (such as pyridyl) and substituted $C_6$ to $C_{10}$ aryl (including substituents such as $CF_3$, $C_1$ to $C_6$ alkoxy, CN).

The embodiments of the process of the present invention is shown in Schemes 1-4:

Scheme 1 illustrates one route to the synthesis of compounds of Formula (I-A) and (I-B), starting from a protected-Corey lactone compound of Formula (X):

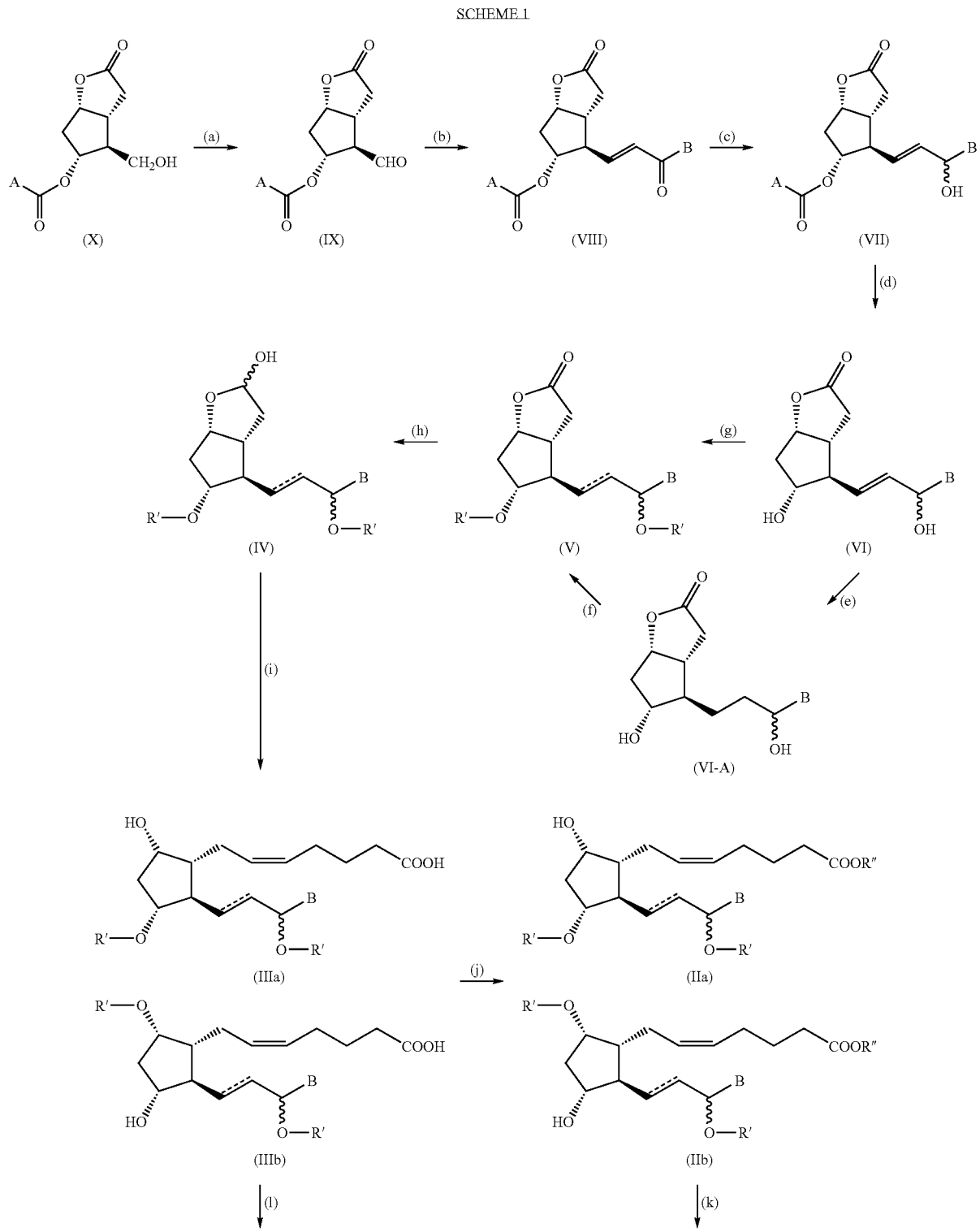

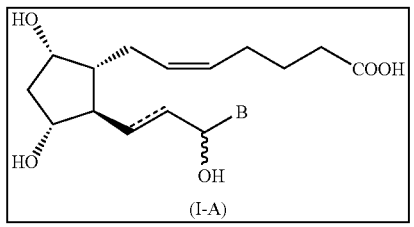

(I-A)

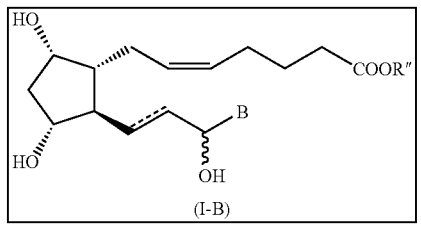

(I-B)

(a) oxidation; (b) modified Homer-Wadsworth-Emmons reaction; (c) reduction; (d) deprotection
(e) hydrogenation; (f) silylation; (g) silylation; (h) reduction; (i) Wittig reaction; (j) alkylation;
(k) deprotection; (l) deprotection In an alternative procedure according to the present invention, the intermediate (VI-A) in Scheme 1 can be made by carrying out steps (a) and (b) as shown in Scheme 1, and substituting steps (c), (d), and (e) in Scheme 1 with the steps (e'), (c') and (d') as shown in the following Scheme 2:

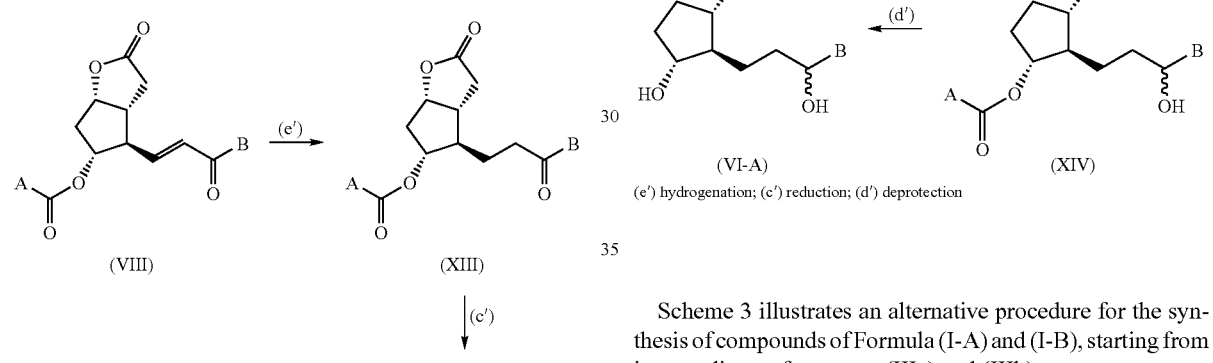

(e') hydrogenation; (c') reduction; (d') deprotection

Scheme 3 illustrates an alternative procedure for the synthesis of compounds of Formula (I-A) and (I-B), starting from intermediates of structure (IIIa) and (IIIb):

SCHEME 3

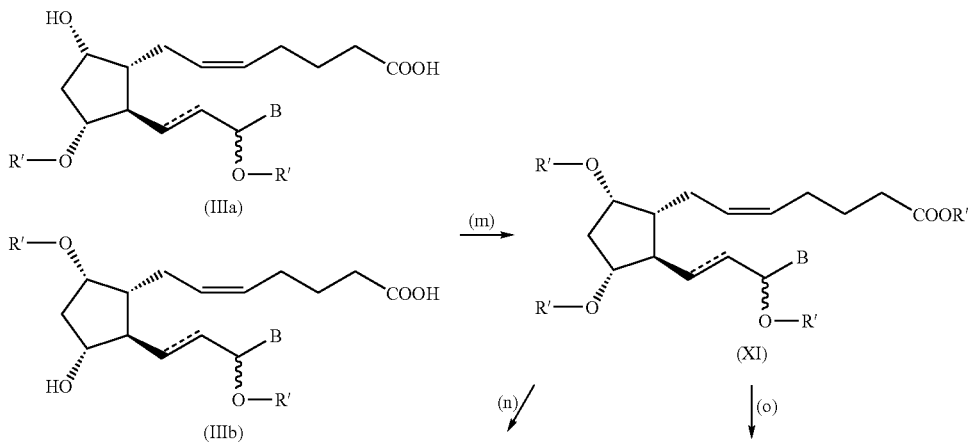

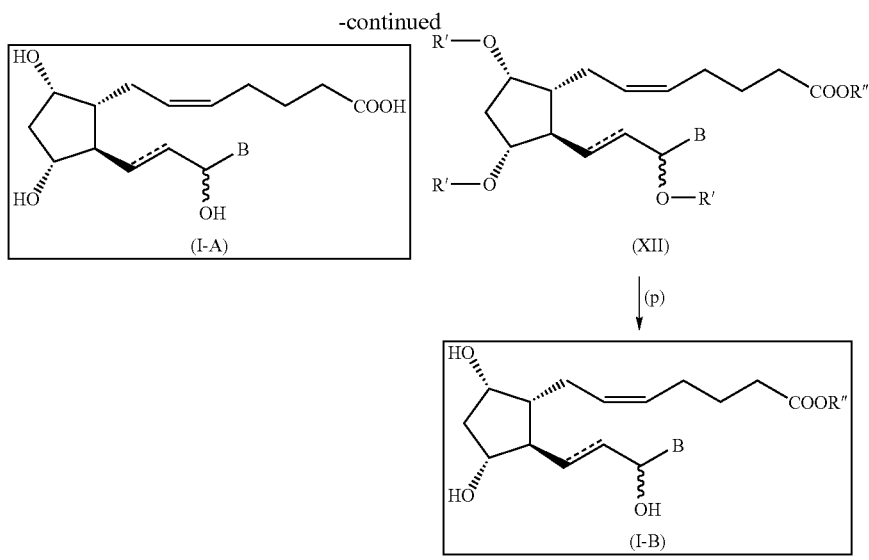

(m) silylation; (n) deprotection; (o) transesterification; (p) deprotection

Scheme 4 shows an alternative procedure for the synthesis of compounds of Formula (I-B) starting from the intermediates of Formula (IIa) and (IIb):

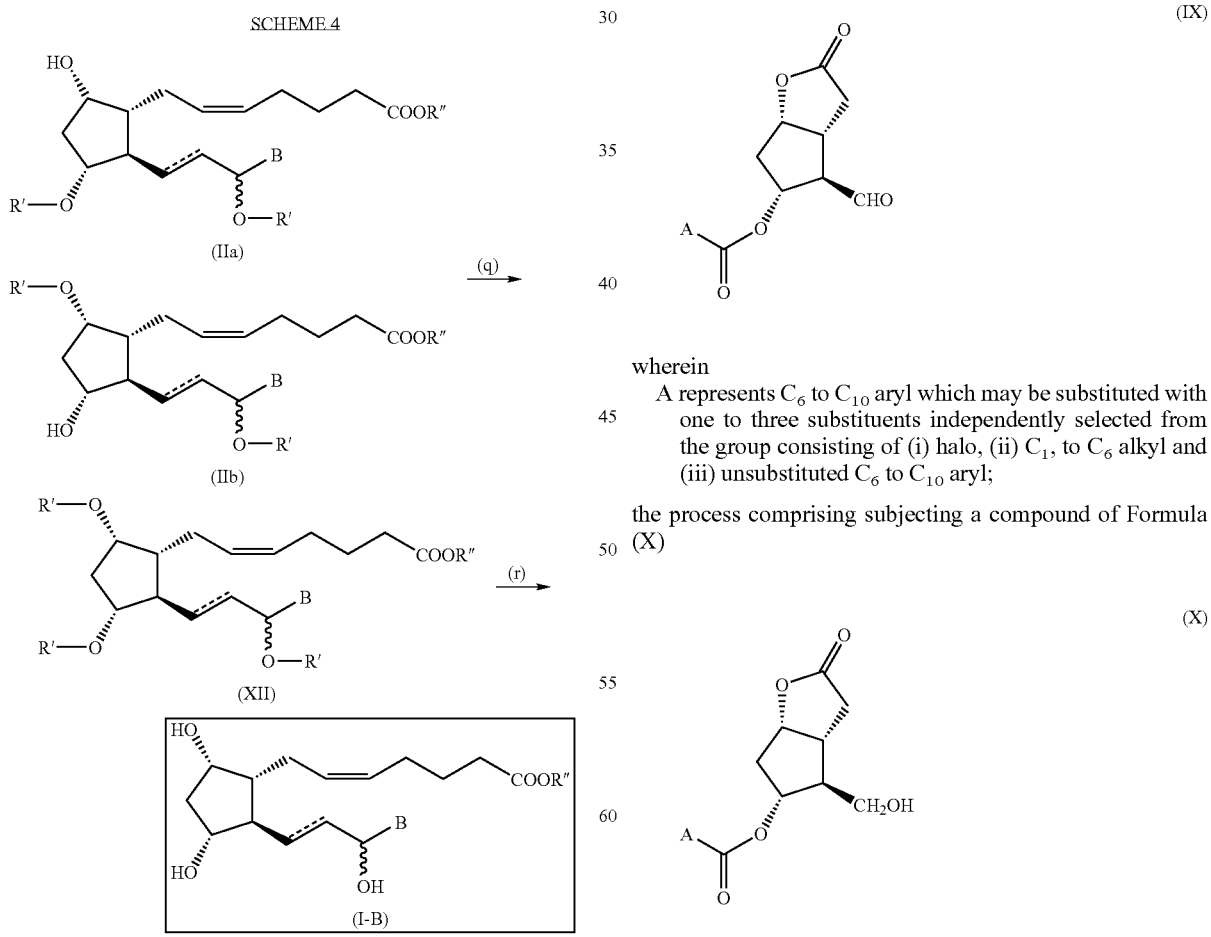

(q) silylation; (r) deprotection

In one aspect of the present invention, there is provided a process for the production of a compound of Formula (IX):

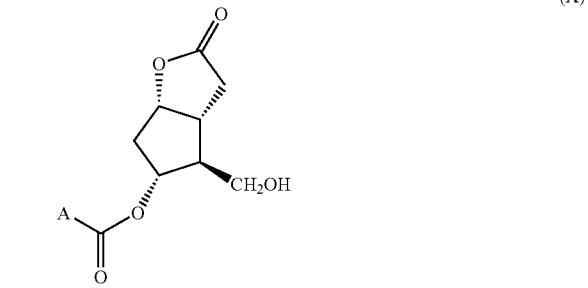

wherein
A represents $C_6$ to $C_{10}$ aryl which may be substituted with one to three substituents independently selected from the group consisting of (i) halo, (ii) $C_1$ to $C_6$ alkyl and (iii) unsubstituted $C_6$ to $C_{10}$ aryl;

the process comprising subjecting a compound of Formula (X)

(X)

to an oxidation reaction in the presence of a catalytic amount of a stable organic nitroxyl radical.

The above reaction may be carried out by electrooxidation in the presence of the organic nitroxyl radical.

Alternatively, the oxidation reaction may be carried out in the presence of a nitroxyl radical and at least one molar equivalent of a co-oxidant selected from the group consisting of m-chloroperbenzoic acid, high-valent metal salts, sodium bromite, sodium or calcium hypochlorite, N-chlorosuccinimide or hypervalent iodine compounds such as [bis(acetoxy) iodo]benzene. Preferably, the co-oxidant is sodium hypochlorite.

The stable organic radical preferably comprises a completely α-substituted piperidin-1-oxy radical, such as 2,2,6,6-tetramethyl-1-piperidinyloxy, free radical (TEMPO, free radical).

Prior art oxidation procedures for oxidising the compound of Formula (X) to form the compound of Formula (IX) include the use of dimethylsulfoxide-dicyclohexylcarbodiimide. However, such a method requires isolation of the aldehyde (IX). Since the aldehyde (IX) is not particularly stable in solution, an amount of decomposition product is usually observed during work-up.

Advantageously, in the present method of oxidation of the compound of Formula (IX) using a stable organic radical such as TEMPO free radical, the aldehyde (IX) solution obtained in this step can be employed in the subsequent step without isolation of the aldehyde, thus minimising any decomposition.

In a further aspect of the present invention, there is provided a process for the production of a compound of Formula (VIII):

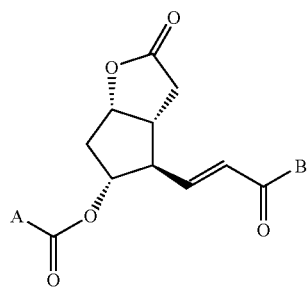

(VIII)

wherein
A represents $C_6$ to $C_{10}$ aryl which may be unsubstituted or substituted with one to three substituents independently selected from the group consisting of (i) halo, (ii) $C_1$ to $C_6$ alkyl and (iii) unsubstituted $C_6$ to $C_{10}$ aryl;
B represents a substituent selected from the group consisting of: (i) $C_1$ to $C_6$ alkyl, (ii) $C_7$ to $C_{16}$ aralkyl, wherein the aryl group may be unsubstituted or substituted with one to three substituents independently selected from the group consisting of $C_1$ to $C_6$ alkyl, halo and $CF_3$ and (iii) —$(CH_2)_n OR^a$, wherein n represents 1, 2 or 3 and $R^a$ represents a $C_6$ to $C_{10}$ aryl group which may be unsubstituted or substituted with one to three substituents independently selected from the group consisting of $C_1$ to $C_6$ alkyl, halo or $CF_3$, the process comprising subjecting a compound of Formula (IX):

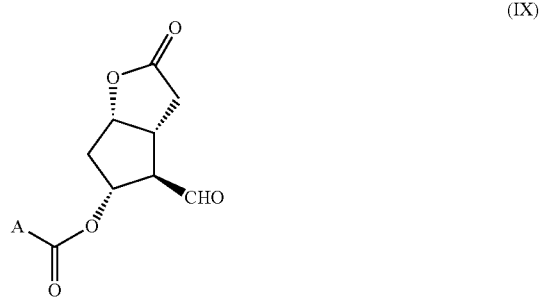

(IX)

to reaction with a phosphonate compound having the structure:

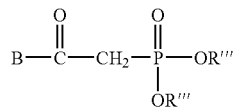

wherein A and B are as defined as above, and each R''' is the same or different (preferably the same) and each represents a $C_1$ to $C_6$ alkyl group (preferably methyl), the process being carried out in the presence of lithium chloride and an organic base (such as tertiary alkylamines, e.g. di-iso-propylethylamine).

The compounds of Formula (IX) are commercially available or can be made from commercially available starting materials. For example, the compound of Formula (IX) may be prepared by the process described in U.S. Pat. No. 3,778,450.

The phosphonate compound of formula:

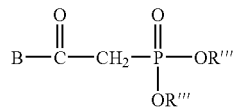

may be produced by methods known in the art [see for example, B. Resul et al., J. Med. Chem. (1993), 36, 243-248)]. As an example, dimethyl-(2-oxo-4-phenylbutyl)phosphonate may be produced from dimethyl-(2-oxo-propyl) phosphonate via the following reaction:

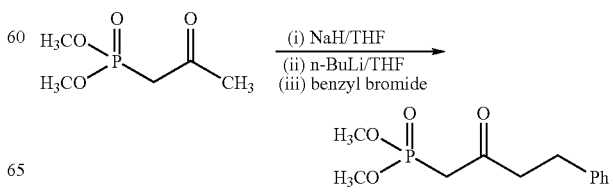

A preferred process for producing the phosphonate compound of formula:

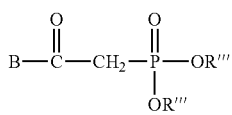

comprises the reaction of a dialkylmethylphosphonate of structure:

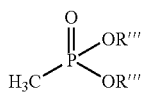

with a strong base (e.g. $^n$BuLi) to generate an anion, followed by reaction of the anion with a compound of formula B—CO$_2$R$^y$, wherein R$^y$ can represent any group that can form a leaving group —OR$^y$. Typical R$^y$ groups include $C_1$ to $C_6$ alkyl, such as methyl, or ethyl (methyl is preferred). Thus the reaction of dimethylmethyl phosphonate (methylphosphonic acid dimethyl ester) with a strong base such as n-butyllithium, to general the corresponding anion, followed by reaction of the anion with a compound of Formula B—CO$_2$R$^y$ is shown below:

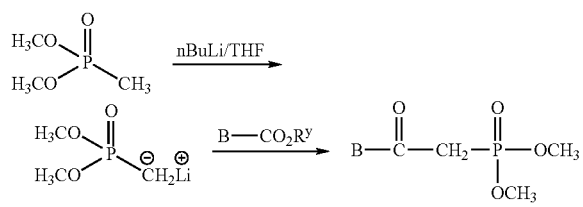

Dimethyl(2-oxo-4-phenylbutyl)phosphonate can be produced in good yield from the following reaction:

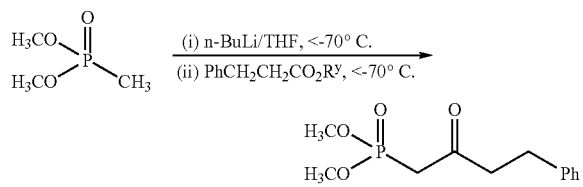

The product from this reaction can be typically purified by distillation. Advantageously, this reaction is usually free of side reactions compared with the prior art process using dimethyl(2-oxopropyl)phosphonate.

The process described above for producing the compound of formula VIII is a modified Horner-Wadsworth-Emmons reaction carried out in milder conditions, in which the usual base used to generate the anion of the phosphonate, sodium hydride in THF or potassium carbonate in toluene, is replaced by a base selected from the group consisting of tertiary alkylamines, such as triethylamine and diisopropylethylamine and DBU [1,8-diazabicyclo(5.4.0)undec-7-ene]. Advantageously, unlike the prior art methods which can lead to poor to moderate yields of the product (VIII), the use of milder reagents, i.e. lithium cations from lithium chloride, in combination with these tertiary alkylamines leads to cleaner reactions with high yield of product.

The reaction is preferably carried out at temperatures in the range of −20° C. to 40° C., and preferably −10° C. to 30° C. Suitable solvents for this reaction include those selected from the group consisting of benzene, toluene, acetonitrile, dichloromethane, diethylether, and mixtures thereof.

In the compound of Formula (VIII), the group A preferably represents an unsubstituted $C_6$ to $C_{10}$ aryl group (e.g. phenyl).

Other preferred substituents for the group A include those selected from $C_6$ to $C_{10}$ aryl group being substituted with one substituent selected from halo or phenyl. Further preferred substituents for the group A include unsubstituted or substituted phenyl wherein the substituent is selected from halo or phenyl. In a preferred process, the group A represents phenyl.

According to another aspect of the present invention, there is provided a process for the production of a compound of Formula (VII):

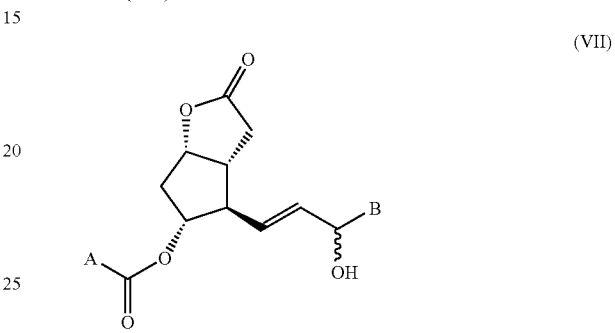

wherein
A represents unsubstituted $C_6$ to $C_{10}$ aryl;
B represents a substituent selected from the group consisting of:
(i) $C_1$ to $C_6$ alkyl, (ii) $C_7$ to $C_{16}$ aralkyl, wherein the aryl group may be unsubstituted or substituted with one to three substituents independently selected from the group consisting of $C_1$ to $C_6$ alkyl, halo and $CF_3$ and (iii) —(CH$_2$)$_n$OR$^a$, wherein n represents 1, 2 or 3 and R$^a$ represents a $C_6$ to $C_{10}$ aryl group which may be unsubstituted or substituted with one to three substituents independently selected from the group consisting of $C_1$ to $C_6$ alkyl, halo or $CF_3$;

the process comprising reducing the oxo group in the side chain of a compound of Formula (VIII):

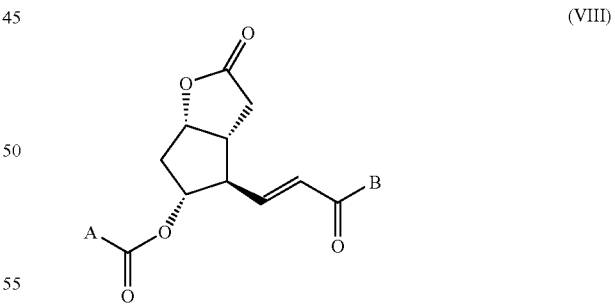

Suitable reducing agents for the reduction of the side chain oxo group include borane-dimethylsulfide complex, lithium tri-sec-butylborohydride, {LiB[CH(CH$_3$)CH(C$_2$H$_5$)$_3$H} (L-Selectride$^{RTM}$) and sodium borohydride. Where the final product is desired as a racemate (such as fluprostenol), a non-stereoselective reducing agent may be used (e.g. LiAlH$_4$, NaBH$_4$ and other metallic hydrides).

Where the final product is desired as a single isomer (e.g. as in latanoprost), the reducing agent suitably comprises borane-dimethylsulfide complex in the presence of a chiral oxazaborolidine catalyst ("Corey catalyst") because of the greater selectivity towards the production of a major amount of the desired isomer. Although this reaction strongly favours the production of the desired isomer, any undesired isomer which may be formed, may be separated by chromatographic techniques, such as flash column chromatography.

Thus, a preferred reagent for the reduction reaction is borane-dimethylsulfide complex in the presence of a chiral oxazaborolidine catalyst (Corey catalyst). In this embodiment of the present invention, the group A in the compound of Formula (VII), in addition to being unsubstituted $C_6$ to $C_{10}$ aryl, can also represent $C_6$ to $C_{10}$ aryl substituted with one to three substituents independently selected from the group consisting of (I) halo, I.e. fluoro, chloro, bromo or iodo, (ii) $C_1$ to $C_6$ alkyl and (iii) $C_6$ to $C_{10}$ aryl, such as phenyl.

The use of borane-dimethylsulfide complex in combination with a Corey catalyst is especially preferred because the reaction takes place with excellent selectivity. In fact, a marked improvement in stereoselectivity is seen compared with the reaction using L-Selectride$^{RTM}$. A further advantage is that the reduction reaction using borane-dimethylsulfide complex can be carried out at a higher temperature (typically $-15°$ C. to $-18°$ C.) compared with L-Selectride$^{RTM}$, which requires a reaction temperature of less than $-70°$ C.

The Corey catalyst comprises a chiral oxazaborolidine compound [see J. Am. Chem. Soc., 109, 5551, (1987) and J. Am. Chem. Soc. 109, 7925, (1987) and references cited in Lancaster Catalogue 2000-2001, page 819] such as (R)-tetrahydro-1-methyl-3,3-diphenyl-1H,3H-pyrrole[1,2-c][1,3,2]oxazaborole, may be prepared by reaction of the appropriate chiral prolinol [such as the commercially available (R)-(+)-α,α-diphenylprolinol] with a trialkyl boroxine, e.g.:

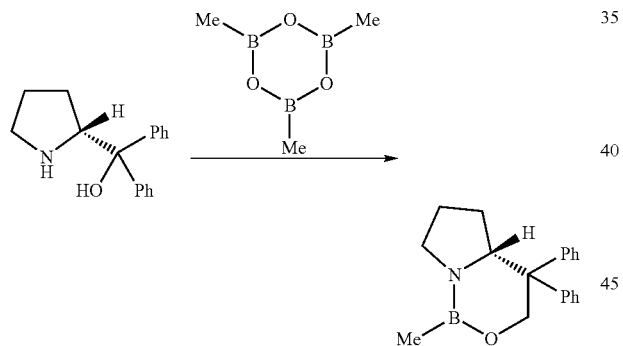

The reaction is carried out in inert conditions in a solvent such as toluene, diethylether or tetrahydrofuran. The oxazaborolidine catalyst is employed as a solution in the reduction step.

According to another aspect of the present invention, there is provided a process for the production of a compound of Formula (V):

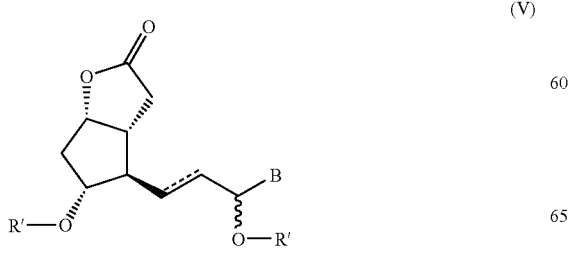

(V)

wherein
the dashed line forms an optional double bond;
B represents a substituent selected from the group consisting of:
(i) $C_1$ to $C_6$ alkyl, (ii) $C_7$ to $C_{16}$ aralkyl, wherein the aryl group may be unsubstituted or substituted with one to three substituents independently selected from the group consisting of $C_1$ to $C_6$ alkyl, halo and $CF_3$ and (iii) —$(CH_2)_nOR^a$, wherein n represents 1, 2 or 3 and $R^a$ represents a $C_6$ to $C_{10}$ aryl group which may be unsubstituted or substituted with one to three substituents independently selected from the group consisting of $C_1$ to $C_6$ alkyl, halo or $CF_3$; and
R' represents the substituent:

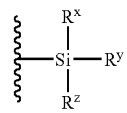

wherein $R^x$, $R^y$ and $R^z$ are the same or different and each independently represents $C_1$ to $C_6$ alkyl, $C_6$ to $C_{10}$ aryl or $C_7$ to $C_{16}$ aralkyl;

the process comprising the steps of:
(a) deprotecting the hydroxyl group of a compound of Formula (VII):

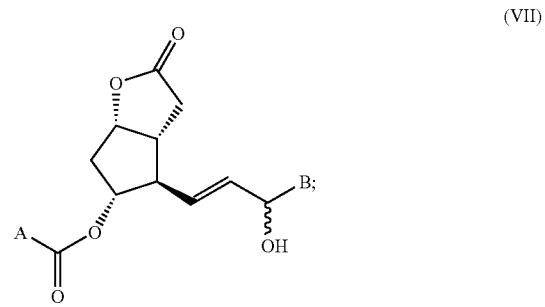

(VII)

wherein A represents $C_6$ to $C_{10}$ aryl which may be unsubstituted or substituted with one to three substituents independently selected from the group consisting of (i) halo, (ii) $C_1$ to $C_6$ alkyl and (iii) unsubstituted $C_6$ to $C_{10}$ aryl;

to form the corresponding hydroxy-substituted compound of Formula (VI):

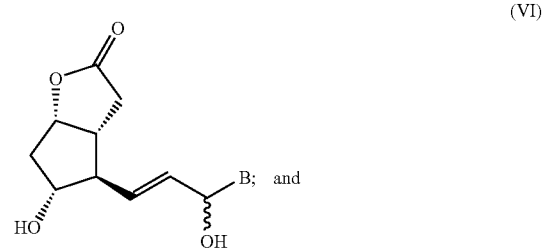

(VI)

(b) optionally, when the dashed line of the compound of Formula (v) represents a single bond, the double bond of the compound of Formula (VI) is hydrogenated to form the compound of Formula (VI-A):

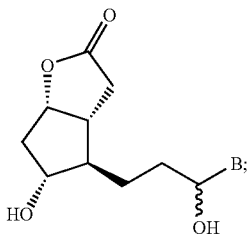

(VI-A)

(c) subjecting a compound of Formula (VI) or (VI-A) to a reaction with a silylating agent having the formula:

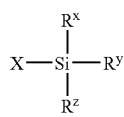

wherein $R^x$, $R^y$ and $R^z$ are as defined above and X represents F, Cl, Br or I.

The deprotection step (a) wherein the protecting group A on the hydroxyl group of the cyclopentane ring is removed, is preferably carried out in the presence of a base. Preferred bases for use in the deprotection reaction includes those selected from the group consisting of $K_2CO_3$, $Na_2CO_3$ and $Li_2CO_3$, with $K_2CO_3$ being particularly preferred.

Suitable solvents for the deprotection reaction include alcohols, such as methanol, ethanol and isopropanol.

The isolation of the deprotected product from step (a) may be carried out by standard chromatography procedures. However, it has been found that the deprotected product can advantageously be isolated by extraction with hexane fractions, thus avoiding the use of time consuming and expensive chromatographic procedures.

For the production of prostaglandin derivatives having one saturated side chain, such as latanoprost described above, it is convenient at this stage, i.e. after the deprotection step (a), to hydrogenate the double bond in the side chain to form the intermediate of Formula (VI-A).

The hydrogenation step can be carried out using any suitable hydrogenation catalyst such as palladium, platinum or rhodium, which may be supported on an inert support, such as carbon. An example of a suitable hydrogenation catalyst is 5% palladium on carbon.

In a preferred procedure, the hydrogenation reaction is carried out in the presence of sodium nitrite, preferably in aqueous solution. This procedure avoids the formation of elimination products and thus results in improved yields (typically greater than 95%) of the compounds of Formula (VI-A). Suitable solvents for the hydrogenation reaction include alcohols such as methanol and ethanol. On completion of the hydrogenation reaction, the mixture is preferably stirred with dilute hydrochloric acid to remove the nitrite (by conversion to nitrous acid, which decomposes at ambient temperature). This procedure ensures that nitrite is not carried through to the subsequent synthetic procedures.

Without wishing to be bound by theory, the role of the sodium nitrite in the hydrogenation reaction is to avoid the formation of elimination products, that is, the elimination of a water molecule from the side chain of the starting material and, as a consequence, formation of the fully saturated deoxygenated analogue of the desired product.

In order to produce the compound of Formula (V), the compound produced in step (a) having the Formula (VI) or the compound produced in step (b) having the Formula (VI-A) is reacted with a silylating agent $(X)Si(R^x)(R^y)(R^z)$. The groups $R^x$, $R^y$, and $R^z$ can be the same or different each represents a $C_1$ to $C_6$ alkyl group or a $C_6$ to $C_{10}$ aryl group. Preferably, each of the groups $R^x$, $R^y$, and $R^z$ are independently selected from methyl, ethyl, butyl, isopropyl. Particularly preferred silylating agents for use in step (c) are selected from the group consisting of trimethylsilyl chloride, triethylsilyl chloride and tert-butyidimethylsilyl chloride. Triethylsilyl chloride is particularly preferred.

The silylation step is preferably carried out in the presence of a base, for example an organic base, such as imidazole or trialkylamines, such as triethylamine.

Suitable solvents for use in the silylation reaction include polar aprotic solvents such as tetrahydrpfuran or dimethylsulfoxide, or chlorinated solvents such as dichloromethane. Preferably, however, the reaction is carried out in a solvent comprising dimethylformamide.

The use of silyl protecting groups in accordance with the present invention is advantageous because it generally results in cleaner reactions, with higher yields compared with reactions wherein the hydroxyl group is not protected.

The use of silyl protecting groups in the present process has particular advantages compared with the prior art process employing, e.g. benzoyl- and para-phenylbenzoyl (PPB)-protecting groups because silyl groups are stable to the subsequent reduction reaction with e.g. DIBAL-H (di-iso-butylaluminium).

In fact, the presence of benzoyl- and PPB-protecting groups prevents the use of many reducing agents, including DIBAL-H, in the subsequent reduction of the lactone ring to form the lactol, because such a reaction can result in the reduction of the oxo moieties in the protecting groups. Thus, in prior art procedures wherein DIBAL is employed as a reducing agent and wherein the starting material comprises benzoyl- or PPB-protecting groups, starting materials must be deprotected prior to the reduction step. However, the presence of unprotected hydroxyl groups in the DIBAL-H reduction step is undesirable because each free hydroxyl group or the starting material coordinates with DIBAL-H. As a result, the use of additional equivalents of DIBAL-H becomes necessary.

A second advantage of using silyl protecting groups in the subsequent Wittig reaction [step (i) in Scheme 1], is that the formation of the desired cis isomer is favoured. Silyl protecting groups have the further advantage in that they generally increase the lipophilic character of the molecules, so that their derivatives are readily soluble in organic solvents. Thus, in the Wittig reaction, removal of the phosphine oxide by-product is facilitated because the silyl-protected Wittig reaction product [(IIIa)/(IIIb)] is soluble in hexane, whereas the triphenylphosphine oxide is insoluble, thus allowing separation by filtration. Subsequent purification of the product can be carried out by silica gel filtration, rather than a full chromatographic purification.

A further advantage of employing silyl protecting groups is that these protecting groups can be removed under mild conditions, as discussed below. Alternatively, the intermediate compound of Formula (V) wherein the solid and dashed lines represent a single bond (i.e. compounds of formula (V-A):

(V-A)

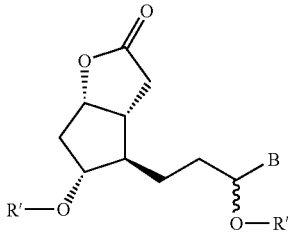

can be made from compounds of Formula (VIII) by a process comprising the steps of:

(a) hydrogenating the double bond of the compound of Formula (VIII):

(VIII)

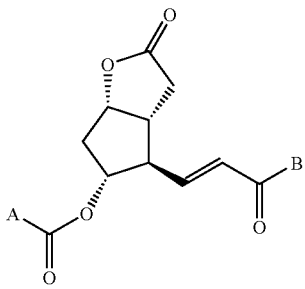

to form a compound of Formula (XIII):

(XIII)

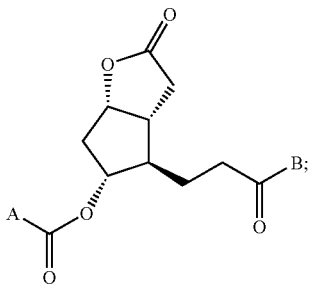

(b) reducing the side chain oxo group of the compound of Formula (XIII) to form a compound of formula (XIV):

(XIV)

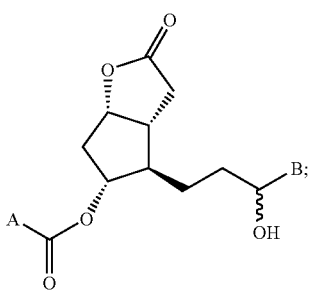

(c) deprotecting the hydroxyl group in the compound of Formula (XIV) to form a compound of formula (VI-A):

(VI-A)

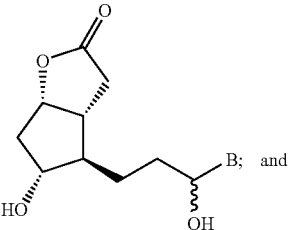

and (d) subjecting the compound of Formula (VI-A) to a reaction with a silylating agent having the formula:

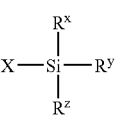

wherein $R^x$, $R^y$ and $R^z$ are as defined above and X represents F, Cl, Br or I.

Steps (a) to (c) of this process are depicted as steps (e'), (c') and (d') in Scheme 2. Step (d) corresponds to step (f) of Scheme 1, the product of which is a compound of Formula (V) wherein the dashed and solid line represents a single bond. The hydrogenation, reduction, deprotection and silylation steps in this alternative procedure are carried out as for the immediately preceding process to form the compounds of Formula (V).

According to another aspect of the present invention, there is provided a process for the preparation of a compound of Formula (IV):

(IV)

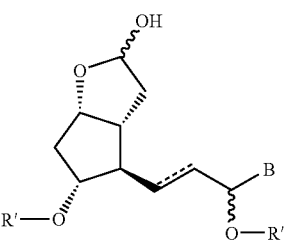

wherein:

the dashed line forms an optional double bond;

B represents a substituent selected from the group consisting of:

(i) $C_1$ to $C_6$ alkyl, (ii) $C_7$ to $C_{16}$ aralkyl, wherein the aryl group may be unsubstituted or substituted with one to three substituents independently selected from the group consisting of $C_1$ to $C_6$ alkyl, halo and $CF_3$ and (iii) —$(CH_2)_nOR^a$, wherein n represents 1, 2 or 3 and $R^a$ represents a $C_6$ to $C_{10}$ aryl group which may be unsubstituted or substituted with one to three substituents independently selected from the group consisting of $C_1$ to $C_6$ alkyl, halo or $CF_3$; and R' represents the substituent:

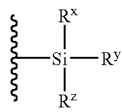

wherein $R^x$, $R^y$ and $R^z$ are the same or different and each independently represents $C_1$ to $C_6$ alkyl, $C_6$ to $C_{10}$ aryl or $C_7$ to $C_{16}$ aralkyl;

the process comprising reducing the lactone oxo group of the compound of Formula (V):

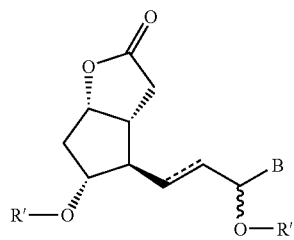

(V)

A suitable reducing agent for this process is di-iso-butylaluminium hydride DIBAL-H), and the reaction may be carried out in e.g. tetrahydrofuran.

According to a further aspect of the present invention there is provided a process for the production of a compound of Formula (IIIa) or (IIIb), or a mixture thereof:

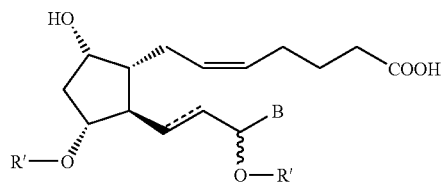

(IIIa)

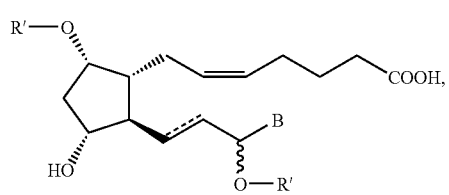

(IIIb)

wherein
the dashed line forms an optional double bond;
B represents a substituent selected from the group consisting of:
(i) $C_1$ to $C_6$ alkyl, (ii) $C_7$ to $C_{16}$ aralkyl, wherein the aryl group may be unsubstituted or substituted with one to three substituents independently selected from the group consisting of $C_1$ to $C_6$ alkyl, halo and $CF_3$ and (iii) $-(CH_2)_nOR^a$, wherein n represents 1, 2 or 3 and $R^a$ represents a $C_6$ to $C_{10}$ aryl group which may be unsubstituted or substituted with one to three substituents independently selected from the group consisting of $C_1$ to $C_6$ alkyl, halo or $CF_3$; and R' represents the substituent:

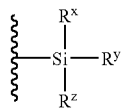

wherein $R^x$, $R^y$ and $R^z$ are the same or different and each independently represents $C_1$ to $C_6$ alkyl, $C_6$ to $C_{10}$ aryl or $C_7$ to $C_{16}$ aralkyl;

the process comprising subjecting a compound of Formula (IV):

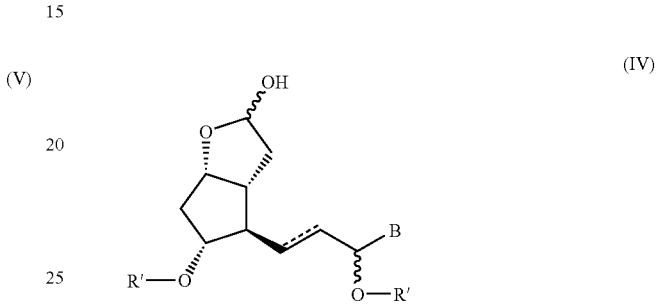

(IV)

to a Wittig reaction with an ylide, the ylide being formed by reaction of a compound of formula:

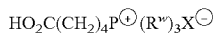

$HO_2C(CH_2)_4P^{\oplus}(R^w)_3X^{\ominus}$ with a strong base, wherein
$R^w$ represents $C_1$ to $C_6$ alkyl or $C_6$ to $C_{10}$ aryl; and
X represents fluoro, chloro, bromo or iodo.
Preferably, the group $R^w$ represents phenyl. The group X preferably represents bromo.
Reagents of formula:

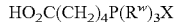

$HO_2C(CH_2)_4P(R^w)_3X$ are commercially available, or can be prepared by reaction of a phosphine, $P(R^w)_3$, with $HO_2C(CH_2)_4-X'$ (wherein X' represents halide, e.g. F, Cl, Br or I). Suitable bases for the forming the ylide include those selected from the group consisting of butyllithium, sodium amide, sodium hydride, and alkali metal alkoxides, including sodium methoxide, sodium ethoxide, potassium ethoxide and potassium tert-butoxide. Potassium tert-butoxide is a particularly preferred base. A suitable solvent for this reaction is tetrahydrofuran.

Thus, in a preferred embodiment, the ylide may be formed by the reaction of (4-carboxybutyl)-triphenylphosphonium bromide with potassium tert-butoxide:

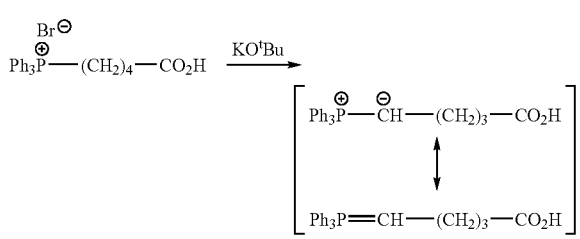

The ylide can be generated using 3 equivalents of the phosphonium halide and 6 equivalents of base, i.e. a ratio of phosphonium halide and base of 1:2, but is preferably generated using 2.15 equivalents of the phosphonium halide and 4 equivalents of base.

During the Wittig reaction, the silyl protecting groups of the hydroxyl substituent on the cyclopentyl ring may migrate to the hydroxyl group formed by the opening of the lactol ring, to result in a mixture of 9- and 11-silylated isomers of Formula (IIIa) and (IIIb).

Although the mixture of compounds (IIIa) and (IIIb) can be separated e.g. by chromatographic procedures, separation is not necessary at this stage because the protecting groups are removed in subsequent reaction steps. Thus, in the process according to the invention, it is preferred that such a mixture of the 9- and 11-silylated isomers (IIIa) and (IIIb) is used in the subsequent reaction step without separation.

In a further aspect of the present invention there is provided a process for the preparation of a compound of Formula (XI):

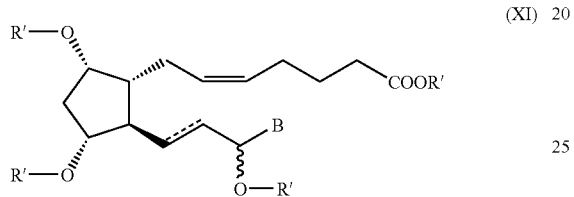

(XI)

wherein
the groups R' are the same and each represents the substituent:

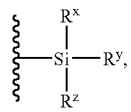

wherein $R^x$, $R^y$ and $R^z$ are the same or different and each independently represents $C_1$ to $C_6$ alkyl, $C_6$ to $C_{10}$ aryl or $C_7$ to $C_{16}$ aralkyl;

the process comprising reacting a compound of Formula (IIIa) or Formula (IIIb), or a mixture thereof, to reaction with a silylating agent having the formula:

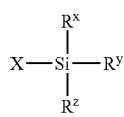

wherein $R^x$, $R^y$ and $R^z$ are as defined above and X represents F, Cl, Br or I.

This procedure is advantageously carried out where a mixture of the compounds of Formula (IIIa) and Formula (IIIb) are formed as the products of the Wittig reaction. The reaction of such a mixture with at least one molar equivalent of a silylating agent, preferably the same silylating agent as is used to protect the hydroxyl groups of the compounds of Formula (V), enables the mixture of compounds of Formula (IIIa) and (IIIb) to be "amalgamated" into a single product of Formula (XI) for subsequent reaction steps. Preferably, in this step, at least a molar equivalent of silylating agent to starting material is employed. Typically, 1.1 to 2 molar equivalents are employed. The formation of a single product allows for better control of subsequent reaction steps and purification.

According to another aspect of the present invention, there is provided a process for the preparation of a compound of Formula (IIa) or (IIb) or a mixture thereof:

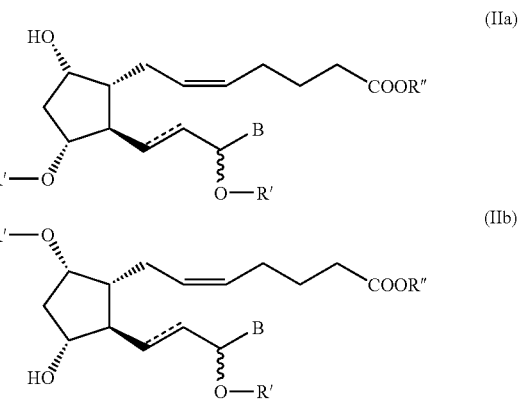

wherein
the dashed line represents an optional double bond;
B represents a substituent selected from the group consisting of:
(i) $C_1$ to $C_6$ alkyl, (ii) $C_7$ to $C_{16}$ aralkyl, wherein the aryl group may be unsubstituted or substituted with one to three substituents independently selected from the group consisting of $C_1$ to $C_6$ alkyl, halo and $CF_3$ and (iii) $-(CH_2)_nOR^a$, wherein n represents 1, 2 or 3 and $R^a$ represents a $C_6$ to $C_{10}$ aryl group which may be unsubstituted or substituted with one to three substituents independently selected from the group consisting of $C_1$ to $C_6$ alkyl, halo or $CF_3$;

R' represents the substituent:

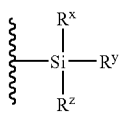

wherein $R^x$, $R^y$ and $R^z$ are the same or different and each independently represents $C_1$ to $C_6$ alkyl, $C_6$ to $C_{10}$ aryl or $C_7$ to $C_{16}$ aralkyl; and
R" represents $C_1$ to $C_8$ alkyl or $C_3$ to $C_8$ cycloalkyl;

the process comprising subjecting a compound of Formula (IIIa) or Formula (IIIb) or a mixture thereof, to reaction with an alkyl halide of formula R"-Hal, wherein R" represents a $C_1$ to $C_6$ alkyl group (such as isopropyl) or a $C_3$ to $C_8$ cycloalkyl group, and "Hal" represents chloro, bromo, or iodo (preferably iodo), in the presence of DBU.

As indicated above, when the Wittig reaction results in migration of the silyl protecting group to form a mixture of 9- and 11-silylated isomers of Formula (IIIa) and (IIIb), the mixture may be alkylated by the process indicated above, to form a mixture of 9- and 11-silylated esters of Formula (IIIa) and (IIIb). Instead of carrying out a silylation of a mixture of compounds of Formula (IIIa) and (IIIb), it is also possible to carry out the silylation after the alkylation step, i.e. on the mixture of compounds of Formula (IIa) and (IIb).

Accordingly, a further aspect of the present invention provides a process for the production of a compound of Formula (XII):

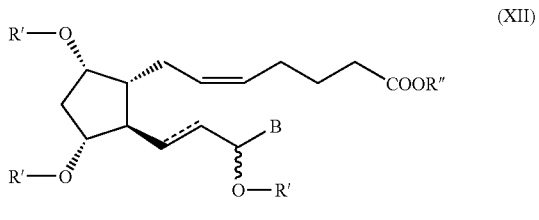

(XII)

wherein
R' represents the substituent:

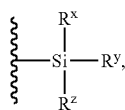

wherein $R^x$, $R^y$ and $R^z$ are the same or different and each independently represents $C_1$ to $C_6$ alkyl, $C_6$ to $C_{10}$ aryl or $C_7$ to $C_{16}$ aralkyl; and
R" represents $C_1$ to $C_6$ alkyl or $C_3$ to $C_8$ cycloalkyl, the process comprising subjecting a compound of Formula (IIa) or Formula (IIb) or a mixture thereof to reaction with at least one molar equivalent of silylating agent having the formula:

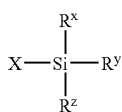

wherein $R^x$, $R^y$ and $R^z$ are as defined above and X represents F, Cl, Br or I.

As indicated above for the silylation of the mixture of compounds of Formula (IIIa) and (IIIb), this process is preferably carried out in the presence of at least a molar equivalent of silylating agent, and even more preferably 1.1 to 2 molar equivalents of silylating agent is employed. Again, this step leads to the "amalgamation" of the mixture of compounds of Formula (IIa) and (IIb) to form a single product [i.e. compounds of Formula (XII)] which facilitates control of subsequent reaction steps and purification of subsequent intermediates.

It has been found that in the steps wherein the mixtures of compound of Formula (IIa) and (IIb) or mixtures of compounds of Formula (IIIa) and (IIIb) are reacted with silylating agents to form single products of Formula (XII) and Formula (XI) respectively (i.e. precursors to the target compounds of Formula IA and IB), purification is facilitated. Advantageously, it has been found that the compounds of Formula (XII) and (XI) can be purified by simply by filtration through silica gel, thus obviating the need to perform a full chromatographic separation, which is particularly undesirable at the late stage of the synthetic process. One reason for this is that the presence of three silyl groups in the compounds of Formula (XII) and (XI) leads to highly lipophilic molecules, which are highly soluble in heptane and thus can be easily separated from the more polar impurities.

According to another aspect of the present invention, there is provided a process for the preparation of a compound of Formula (XII):

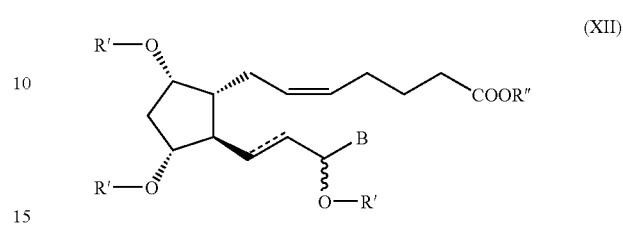

(XII)

wherein:
R' is the same and each represents the substituent:

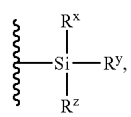

wherein $R^x$, $R^y$ and $R^z$ are the same or different and each independently represents $C_1$ to $C_6$ alkyl, $C_6$ to $C_{10}$ aryl or $C_7$ to $C_{16}$ aralkyl; and
R" represents $C_1$ to $C_6$ alkyl or $C_3$ to $C_8$ cycloalkyl;

the process comprising subjecting a compound of Formula (XI):

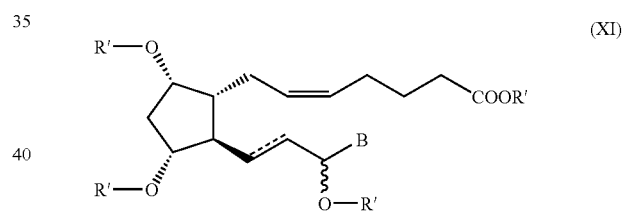

(XI)

wherein the groups R' are preferably the same and each represents the substituent:

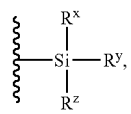

wherein $R^x$, $R^y$ and $R^z$ are the same or different and each independently represents $C_1$ to $C_8$ alkyl, $C_6$ to $C_{10}$ aryl or $C_7$ to $C_{16}$ aralkyl;

to a reaction with an alcohol, having the formula R"—OH, wherein R" represents a $C_1$ to $C_6$ alkyl group (e.g. isopropanol) or $C_3$ to $C_8$ cycloalkyl (e.g. cyclohexanol).

The above process may be carried out optionally in the presence of a weak add catalyst, such as pyridinium p-toluenesulfonate. The reaction should be carried out in the absence of water, to avoid deprotection of the silyl groups.

According to a further aspect of the present invention, there is provided a process for the production of a compound of Formula (I-A):

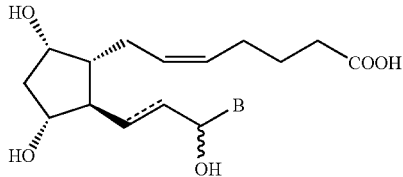

(I-A)

wherein
B represents a substituent selected from the group consisting of:
(i) $C_1$ to $C_6$ alkyl, (ii) $C_7$ to $C_{16}$ aralkyl, wherein the aryl group may be unsubstituted or substituted with one to three substituents independently selected from the group consisting of $C_1$ to $C_6$ alkyl, halo and $CF_3$ and (iii) —$(CH_2)_nOR^a$, wherein n represents 1, 2 or 3 and $R^a$ represents a $C_6$ to $C_{10}$ aryl group which may be unsubstituted or substituted with one to three substituents independently selected from the group consisting of $C_1$ to $C_6$ alkyl, halo or $CF_3$;

the process comprising removing the silyl protecting groups, R', from a compound selected from the group consisting of
(i) a compound of Formula (IIIa), Formula (IIIb) or a mixture thereof:

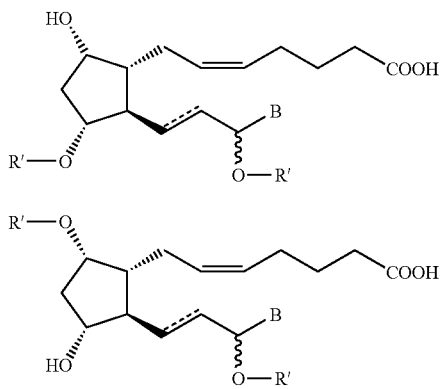

(IIIa)

(IIIb)

(ii) a compound of Formula (XI):

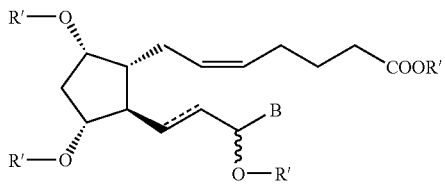

(XI)

wherein B and R' are as defined above.

According to another aspect of the present invention, there is provided a process for the production of a compound of Formula (I-B):

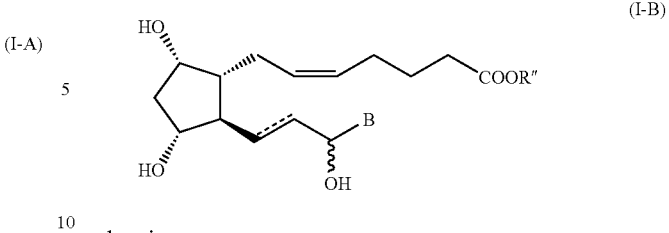

(I-B)

wherein
B represents a substituent selected from the group consisting of:
(i) $C_1$ to $C_6$ alkyl (ii) $C_7$ to $C_{16}$ aralkyl, wherein the aryl group may be unsubstituted or substituted with one to three substituents independently selected from the group consisting of $C_1$ to $C_6$ alkyl, halo and $CF_3$ and (iii) —$(CH_2)_nOR^a$, wherein n represents 1, 2 or 3 and $R^a$ represents a $C_6$ to $C_{10}$ aryl group which may be unsubstituted or substituted with one to three substituents independently selected from the group consisting of $C_1$ to $C_6$ alkyl, halo or $CF_3$; and
R" represents $C_1$ to $C_6$ alkyl or $C_3$ to $C_8$ cycloalkyl;

the process comprising removing the silyl protecting groups R' from a compound selected from the group consisting of:
(i) a compound of Formula (IIa) or (IIb) or a mixture thereof:

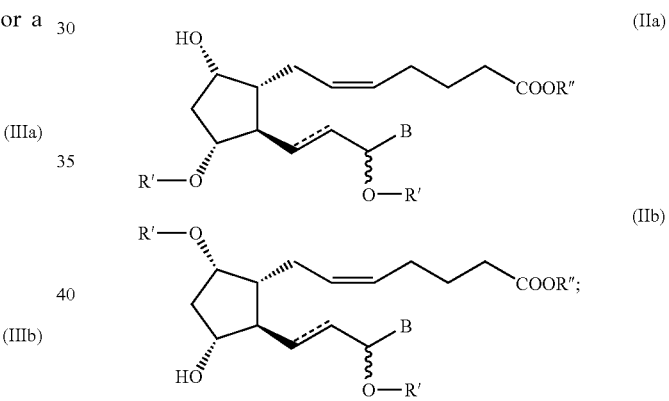

(IIa)

(IIb)

and
(ii) a compound of Formula (XII):

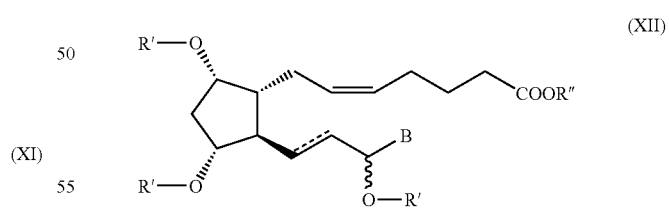

(XII)

wherein B and R" are as defined as above.

The deprotection of the silyl protecting groups R' is advantageously carried out in mild reaction conditions. Suitable reagents for removal of the silyl groups from the compounds of Formula (IIIa), (IIIb), (XI), (IIa), (IIb) and (XII) include weak acids such as acetic acid and citric acid. An especially preferred weak acid is pyridinium p-toluenesulfonate.

The reaction may be carried out in any suitable solvent or solvent mixtures. An especially preferred solvent for the deprotection reaction comprises acetone and water.

In accordance with preferred embodiments of the present invention, the compounds of Formulae (VII), (VI), (VI-A), (V), (IV), (IIIa), (IIIb), (IIa), (IIb), (I-A), (I-B), (XI), (XII) and (XIV) are single enantiomers (i.e. the wavy line in the side chain represents ━━▶ or ·······⫶⫶⫶).

As discussed above, such compounds can be made by using a stereoselective reducing agent [e.g. borane-dimethylsulfide complex in the presence of a chiral oxazaborolidine (Corey) catalyst] in step (c) of Scheme 1, or step (c') in Scheme 2.

In accordance with preferred embodiments of the present invention, the group B in the compounds of Formula (XII), (XI), (VIII), (VII), (VI), (VI-A), (V), (IV), (IIIa), (IIIb), (IIa), (IIb), (I-A) or (I-B) is selected from the group consisting of (i) $C_1$ to $C_6$ alkyl, (ii) $C_7$ to $C_{16}$ aralkyl wherein the aryl group is unsubstituted and (iii) —$(CH_2)_n OR^a$, wherein n represents 1, 2 or 3 and $R^a$ represents a $C_6$ to $C_{10}$ aryl group which is substituted with a substituent selected from halo or $CF_3$.

Even more preferred are compounds of Formula (XII), (XI), (VIII), (VII), (VI), (VI-A), (V), (IV), (IIIa), (IIIb), (IIa), (IIb), (I-A) or (I-B) wherein B is selected from the group consisting of (i) $C_1$ to $C_6$ straight chain alkyl, (ii) —$(CH_2)_2 Ph$ and (iii) —$CH_2 OR^a$, wherein $R^a$ represents a phenyl group substituted with a chloro or $CF_3$ group.

Especially preferred are compounds of Formula (XII), (XI), (VIII), (VI), (VI), (VI-A), (V), (IV), (IIIa), (IIIb), (IIa), (IIb), (I-A) or (I-B) wherein B represents a substituent selected from the group consisting of:

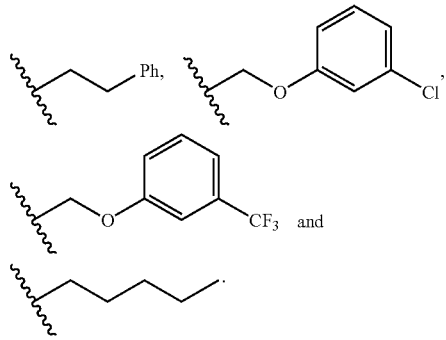

In a further preferred embodiment of the present invention, the solid and dashed lines in each of Formulae (XII), (XI) (V), (IV), (IIIa), (IIIb), (IIa), (IIb), (I-A) and (I-B) forms a single bond.

In yet another preferred embodiment, the solid and dashed lines in each of Formulae (XII), (XI) (V), (IV), (IIIa), (IIIb), (IIa), (IIb), (I-A) and (I-B) forms a double bond.

For the compounds of Formulae (XII), (XI) (V), (IV), (IIIa), (IIIb), (IIa), (IIb), (I-A) and (I-B) wherein the solid and dashed line represents a single bond, B preferably represents —$CH_2 CH_2 Ph$.

For the compounds of Formulae (XII), (XI) (V), (IV), (IIIa), (IIIb), (IIa), (IIb), (I-A) and (I-B) wherein the dashed line represents a double bond, B preferably represents a substituent selected from the group consisting of:

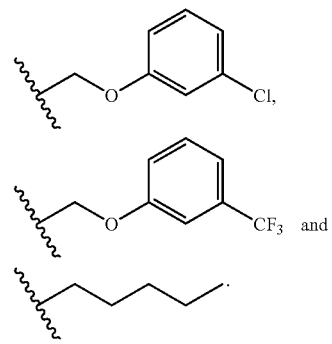

As will be appreciated by a person of skill in the art, the process of the present invention is generally applicable for the synthesis of prostaglandins and prostaglandin analogues, particularly $PGF_{2\alpha}$ and analogues thereof. The process is particularly useful for the production of a compound selected from the group consisting of:

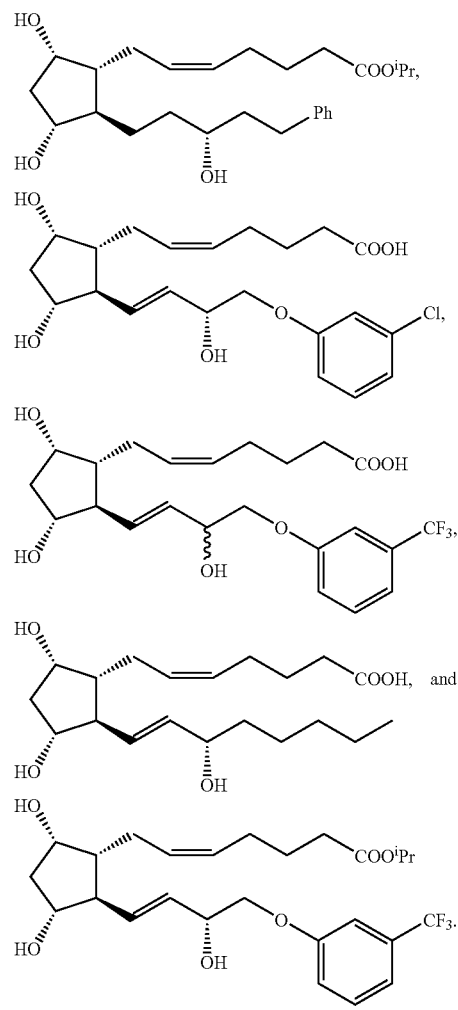

In a preferred embodiment, the present invention provides a process for the synthesis of latanoprost comprising the steps of:

(1) subjecting a compound of Formula (X):

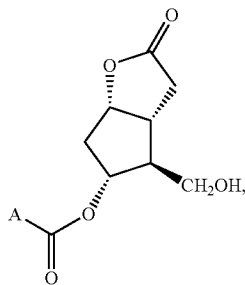
(X)

wherein A represents a $C_6$ to $C_{10}$ aryl group, preferably phenyl, which may be substituted with one to three substituents independently selected from the group consisting of (i) halo, (ii) $C_1$ to $C_6$ alkyl and (iii) unsubstituted $C_6$ to $C_{10}$ aryl,
to an oxidation reaction with sodium hypochlorite, the oxidation reaction being carried out in the presence of a catalytic amount of a stable organic nitroxyl radical (preferably TEMPO free-radical), to form a compound of Formula (IX):

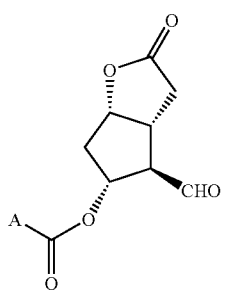
(IX)

(2) subjecting the compound of Formula (IX) as defined above to reaction with a compound having the structure:

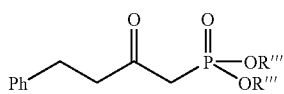

wherein each R''' the same or different and each represents a $C_1$ to $C_6$ alkyl group (preferably methyl), in the presence of lithium chloride and an organic base, to form the compound of Formula (VIII) wherein B is —$CH_2CH_2Ph$:

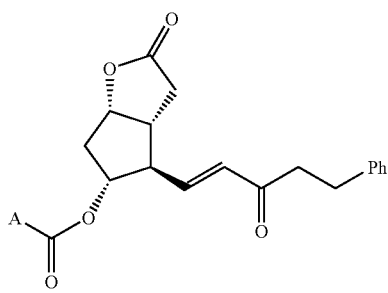

(3) reducing the side chain oxo group of the compound of Formula (VIII) using borane-dimethylsulfide complex, the reduction being carried out in the presence of a chiral oxazaborolidine catalyst, such as (R)-tetrahydro-1-methyl-3,3-diphenyl-1H,3H-pyrrole[1,2c][1,3,2]oxazaborole, to form a compound of Formula (VIII) wherein B is —$CH_2CH_2Ph$:

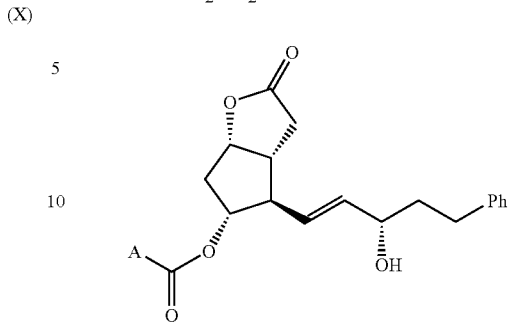

(4) deprotecting the hydroxyl group of the compound of Formula (VII), preferably using $K_2CO_3$ in methanol, to form the compound of Formula (VI) wherein B is —$CH_2CH_2Ph$:

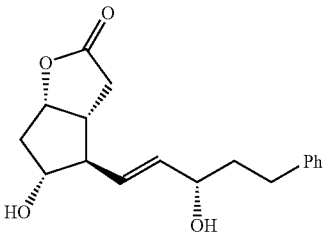

(5) hydrogenating the double bond of a compound of Formula (VI) in the presence of a hydrogenation catalyst (such as palladium, platinum or rhodium), the reaction optionally being carried out in the presence of sodium nitrite, to form a compound of Formula (VI-A) wherein B is —$CH_2CH_2Ph$:

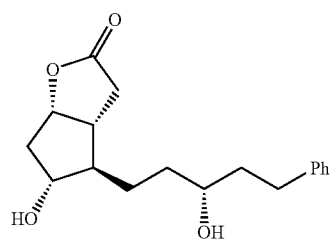

(6) subjecting the compound of Formula (VI-A) to reaction with a silylating agent of formula

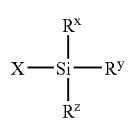

wherein $R^x$, $R^y$ and $R^z$ are as defined as above (a particularly preferred silylating agent being triethylsilyl chloride) as defined above to form a compound of Formula (V) wherein B is —$CH_2CH_2Ph$:

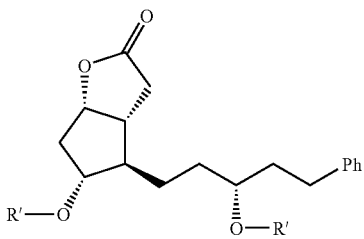

wherein R' represents:

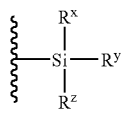

(7) reducing the side chain oxo group of the compound of Formula (V), using a reducing agent such as DIBAL-H, to form a compound of Formula (IV) wherein B is —CH₂CH₂Ph:

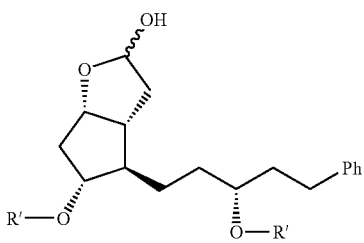

(8) subjecting the compound of Formula (IV) to a Wittig reaction with an ylide, the ylide being formed from the reaction of a compound of formula

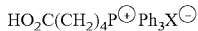

wherein X represents F, Cl, Br or I, with a strong base (such as potassium t-butoxide), to form a compound of Formula (IIIa) or (IIIb) wherein B is —CH₂CH₂Ph:

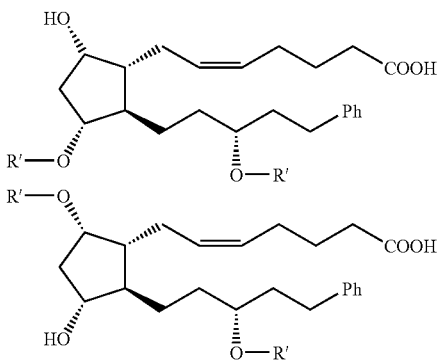

or a mixture thereof;

(9) alkylating the carboxylic acid group of the compound of Formula (IIIa) or (IIIb), or a mixture thereof, with isopropyl iodide in the presence of DBU, to form the compound of Formula (IIa) or (IIb), wherein B is —CH₂CH₂Ph and R" is isopropyl:

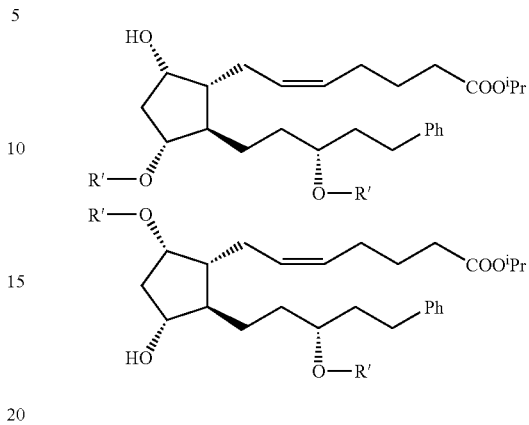

or a mixture thereof; and

(10) removing the protecting groups from the compound of Formula (IIa) or (IIb), or a mixture thereof, to form latanoprost:

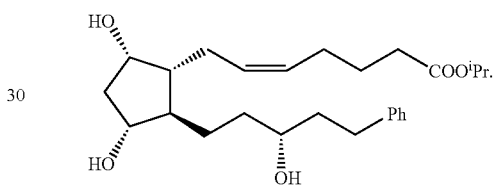

The above steps (1) to (10) correspond to steps (a)-(b)-(c)-(d)-(e)-(f)-(h)-(i)-(j)-(k) in Scheme 1 above.

In an alternative process, latanoprost can be formed by a procedure involving carrying out steps (1) and (2) of the preceding process, replacing steps (3), (4) and (5) with the following steps (3'), (4') and (5'), and thereafter carrying out steps (6-(10) as described in the preceding process. Steps (3'), (4') and (5') are as follows:

(3') subjecting the double bond of the compound of Formula (VIII) to a hydrogenation reaction in the presence of a hydrogenation catalyst (e.g. palladium, platinum or rhodium), the reaction being carried out optionally in the presence of sodium nitrite, to form a compound of Formula (XIII) wherein B is —CH₂CH₂Ph:

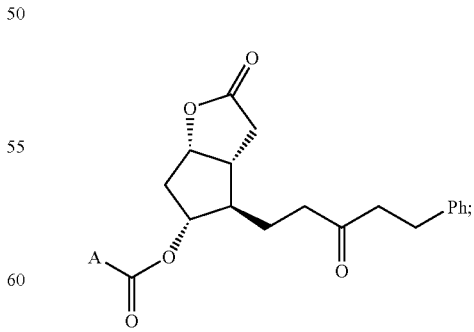

(4') reducing the side chain oxo group of the above compound of Formula (XIII) using borane-dimethylsulfide complex, the reduction being carried out in the presence of a chiral oxazaborolidine catalyst, such as (R)-tetrahydro-1-methyl-3,3-diphenyl-1H,3H-pyrrole[1,2c]-[1,3,2]ox-
azaborole, to form a compound of Formula (XIV) wherein
B is —CH$_2$CH$_2$Ph:

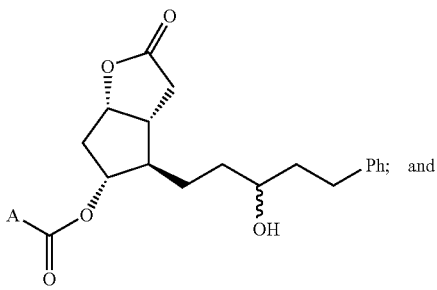

(5') deprotecting the hydroxyl group of the compound of the
above compound of Formula (XIV), preferably using
K$_2$CO$_3$ in methanol, to form a compound of Formula (VI),
wherein the dashed and solid lines represent a single bond,
and B is —CH$_2$CH$_2$Ph:

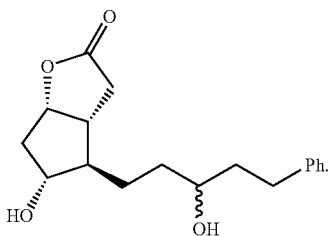

This procedure corresponds to steps (a)-(b)-(e')-(c')-(d')-
(f)-(h)-(i)-(j)-(k) depicted in Scheme 1 and Scheme 2.

In a further preferred embodiment, there is provided a
process for the synthesis of latanoprost comprising carrying
out steps (1) to (8) according to either of the preceding procedures, to form a mixture comprising the compounds of
Formula (IIIa) and Formula (IIIb) having the respective structures:

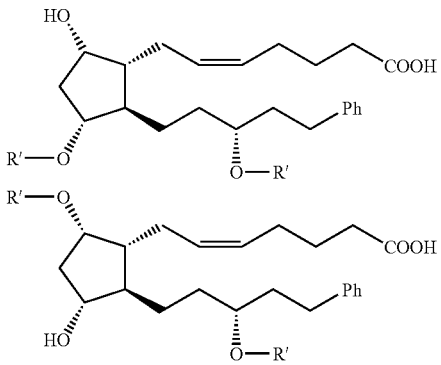

and further carrying out the steps of:
(9a) subjecting said mixture to reaction with at least one
molar equivalent (preferably at least a molar equivalent,
and more preferably 1.1 to 2 molar equivalents) of silylating agent to form a compound of Formula (XI) having the
structure:

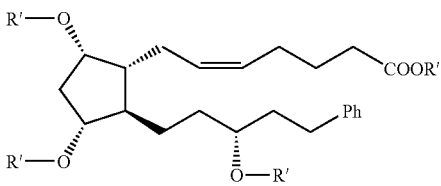

wherein each R' is as defined as above;
(10a) subjecting the compound of Formula (XI) to a transesterification reaction with isopropanol optionally in the
presence of a weak acid catalyst such as pyridinium p-toluenesulfonate, to form the compound of Formula (XII) having the structure:

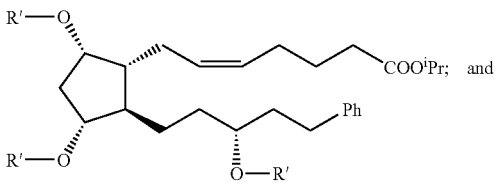

(11a) removing the protecting groups R' to form latanoprost.
These steps (9a) to (11a) correspond to steps (m)-(o)-(p) in
Scheme 2 above.

According to a still further embodiment of the present
process, there is provided a process for the production of
latanoprost comprising carrying out steps (1) to (9) to form a
mixture comprising the compounds of Formula (IIa) and
Formula (IIb) having the respective structures:

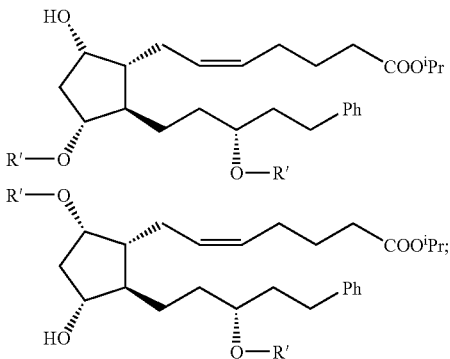

and carrying out the further steps of:
(10b) subjecting said mixture to reaction with at least one
molar equivalent (preferably at least 1.1 molar equivalents,
and more preferably 1.15 to 2 molar equivalents) of silylating agent to form a compound of Formula (XII) having
the structure:

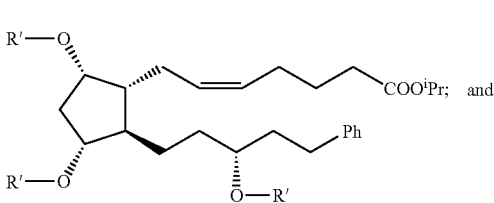

(11b) removing the protecting groups R' to form latanoprost.
The above steps (10b) and (11b) correspond to steps (q)-(r)
shown in Scheme 3 above.

According to a further aspect of the present invention, there are provided novel intermediates for the synthesis of a compound of Formula (I-A) or (I-B) as defined above. The novel intermediates include the following:

compounds of the Formula (VIII):

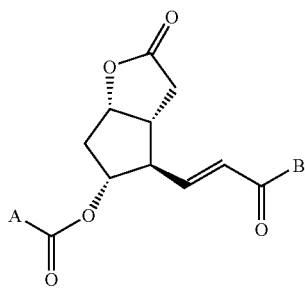

(VIII)

wherein

A represents unsubstituted $C_6$ to $C_{10}$ aryl; and

B represents a substituent selected from the group consisting of: (i) $C_1$ to $C_6$ alkyl, (ii) $C_7$ to $C_{16}$ aralkyl, wherein the aryl group may be unsubstituted or substituted with one to three substituents independently selected from the group consisting of $C_1$ to $C_6$ alkyl, halo and $CF_3$; and (iii) —$(CH_2)_n OR^a$, wherein n represents 1, 2 or 3 and $R^a$ represents a $C_6$ to $C_{10}$ aryl group which may be unsubstituted or substituted with one to three substituents independently selected from the group consisting of $C_1$ to $C_6$ alkyl, halo or $CF_3$.

compounds of the Formula (VII):

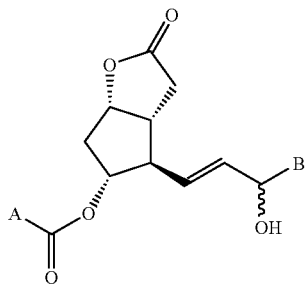

(VII)

and single enantiomers thereof, wherein A and B are as defined herein;

compounds of the Formula (VI):

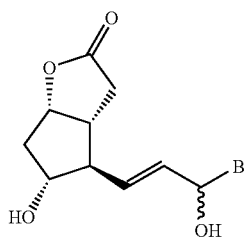

(VI)

and single enantiomers thereof wherein B is as defined herein;

compounds of the Formula (VI-A):

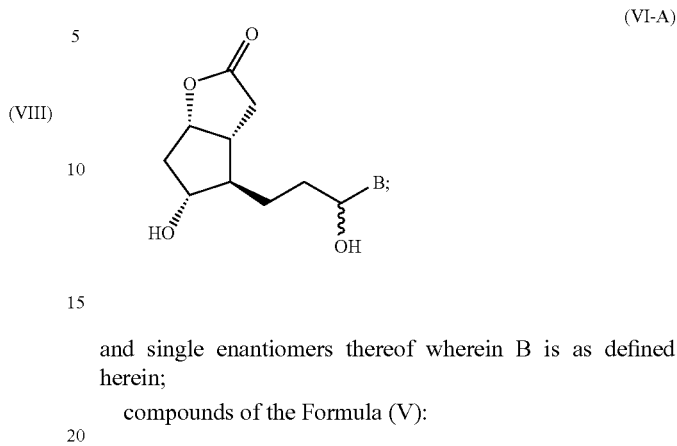

(VI-A)

and single enantiomers thereof wherein B is as defined herein;

compounds of the Formula (V):

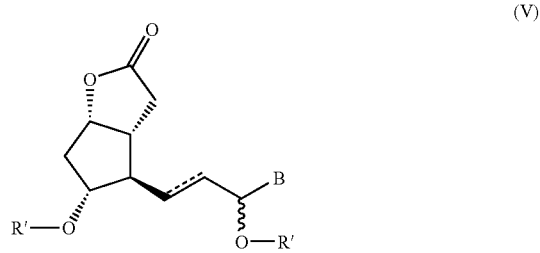

(V)

and single enantiomers thereof wherein B is as defined herein and R' represents the substituent:

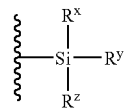

wherein $R^x$, $R^y$ and $R^z$ are the same or different and each independently represents $C_1$ to $C_6$ alkyl, $C_6$ to $C_{10}$ aryl or $C_7$ to $C_{16}$ aralkyl;

compounds of the Formula (IV):

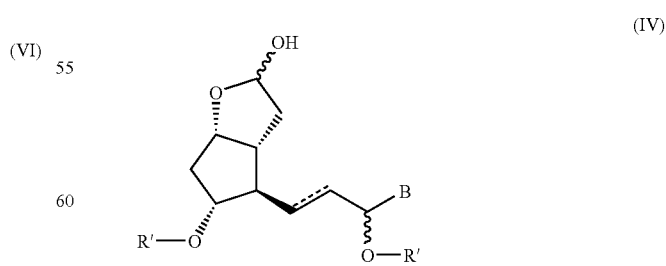

(IV)

and single enantiomers thereof wherein B and R' are as defined herein;

compounds of the Formula (IIIa) or (IIIb):

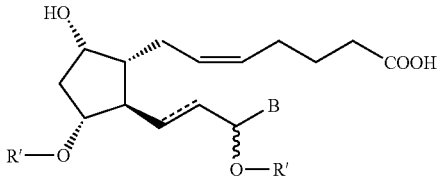
(IIIa)

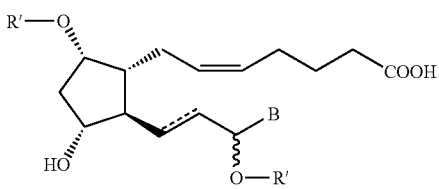
(IIIb)

and single enantiomers, and mixtures thereof wherein B and R' are as defined herein;

compounds of the Formula (IIa) or (IIb):

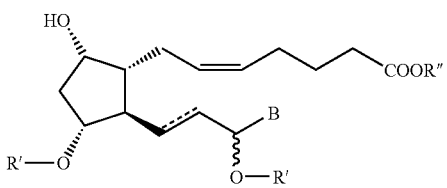
(IIa)

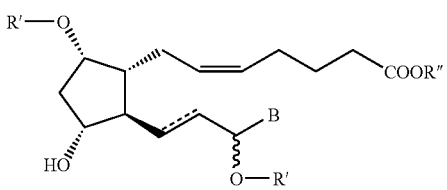
(IIb)

and single enantiomers and mixtures thereof wherein B, R' and R'' are as defined herein;

compounds of the Formula (XI):

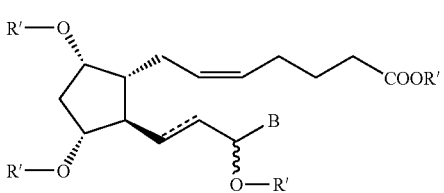
(XI)

and single enantiomers thereof wherein B and R' are as defined herein;

compounds of the Formula (XII):

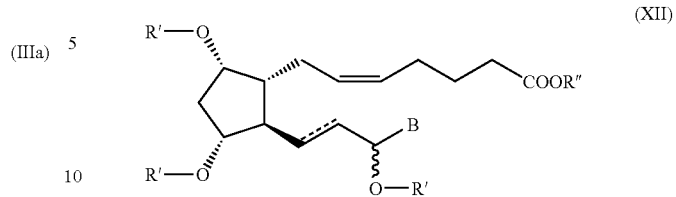
(XII)

and single enantiomers thereof wherein B and R' are as defined herein;

compounds of Formula XIII:

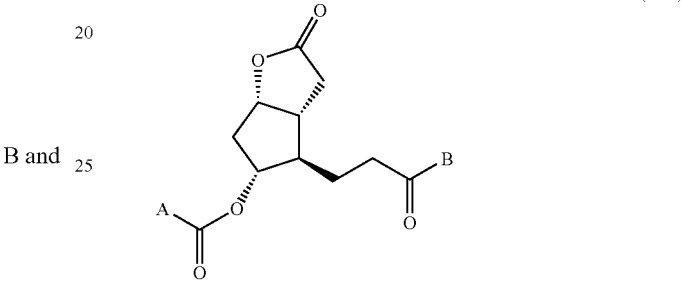
(XIII)

wherein A represents unsubstituted $C_6$ to $C_{10}$ aryl, and B is as defined herein; and compounds of Formula (XIV):

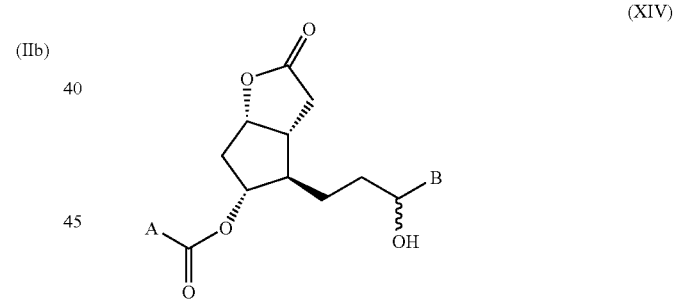
(XIV)

and single enantiomers thereof wherein A represents unsubstituted $C_6$ to $C_{10}$ aryl and B is as defined herein.

Preferably, in any of the structures herein, the group A represents phenyl.

In accordance with preferred embodiments of the present invention, the compounds of Formulae (VII), (VI), (VI-A), (V), (IV), (IIIa), (IIIb), (IIa), (IIb), (XI), (XII), (XIII) and (XIV) are single enantiomers (i.e. the wavy line in the side chain represents ▬◀ or ·······).

In the intermediates of Formula (VIII), (VII), (VI), (VI-A), (V), (IV), (IIIa), (IIIb), (IIa), (IIb), (X), (XI), (XII) and (XIV) the group B is selected from:

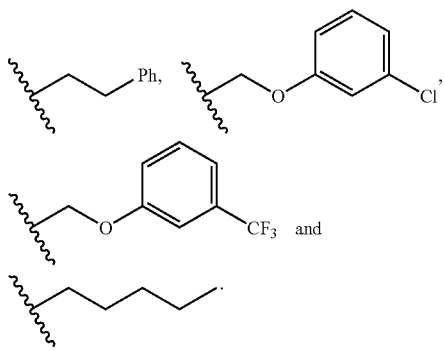

Preferably, for the intermediates of Formula (V), (IV), (IIIa), (IIIb), (IIa), (IIb), (XI) and (XII), the solid and dashed lines represent a single bond and B represents —CH$_2$CH$_2$Ph.

Further preferred are intermediates of Formula (V), (IV), (IIIa), (IIIb), (IIa), (IIb), (XI) and (XII) wherein the solid and dashed lines represent a double bond and B represents a substituent selected from the group consisting of:

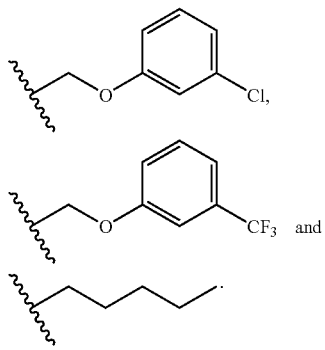

In the intermediates of Formula (V), (IV), (IIIa), (IIIb), (IIa), (IIb), (XI) and (XII), the group R' is preferably:

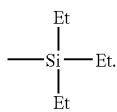

In the compounds of Formula (XII), (IIa), (IIb) and (I-B), the group R" preferably represents isopropyl.

The present invention further provides the use of any novel intermediate as defined as above in the manufacture of latanoprost and the use of any novel intermediate as defined as above in the manufacture of cloprostenol, fluprostenol, PGF$_{2\alpha}$, travoprost, or a PGF (preferably PGF$_{2\alpha}$) analogue.

The present invention also provides the use of a silylating reagent of formula

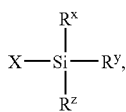

wherein the group X represents F, Cl, Br or I and R$^x$, R$^y$ and R$^z$ are as previously defined, for protecting a hydroxyl group of an intermediate in the synthesis of a prostaglandin or prostaglandin analogue, such as prostaglandin or prostaglandin analogues based on PG-A, PG-B, PG-C PG-D or PGF. The use of these silylating agents is particularly suitable in the synthesis of prostaglandin PGF$_{2\alpha}$ or prostaglandin analogues based on PGF$_{2\alpha}$, including latanoprost, cloprostenol, fluprostenol and travoprost. Of these, latanoprost is particularly preferred.

Preferred R$^x$, R$^y$ and R$^z$ are methyl, ethyl and tert-butyl. A particularly preferred silylating reagent is triethylsilylchloride.

Whilst the above processes and steps refer to PGF$_{2\alpha}$ and analogues thereof, it will also be understood by a person of skill in the art that the process and steps could be successfully applied to the synthesis of other prostaglandin analogues, for example,

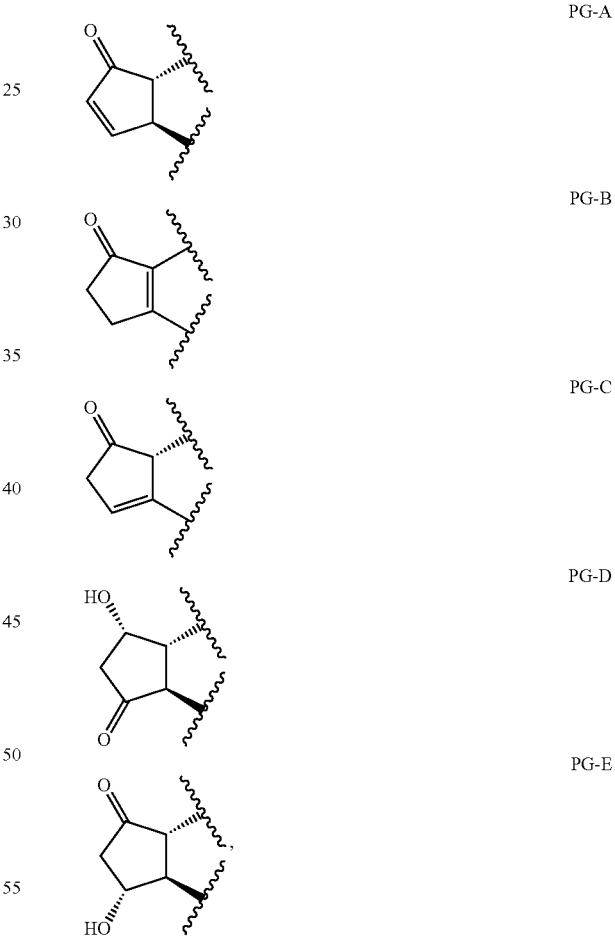

by the provision of one or more additional reaction steps in order to modify the functional groups on the cyclopentyl ring—for example, oxidation of the cyclopentyl ring oxo groups in the PGF derivatives would result in either the PGD or PGE analogues.

As used herein hatched lines attached to the cyclopentane ring indicate bonds that are below the plane of the ring (i.e. bonds in an alpha configuration). Solid wedges attached to the cyclopentane ring indicate bonds that are above the plane of the ring (rings in the beta configuration). It is to be understood that a wavy line, i.e.

represents bonds in either the alpha or beta configuration, and includes single enantiomers, i.e.:

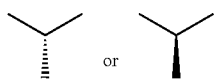

or mixtures thereof, including racemic mixtures. Thus:

Formula (XIV) includes:

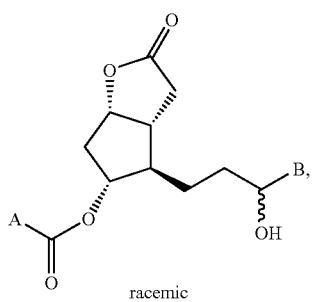

racemic

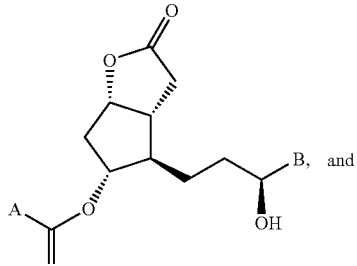

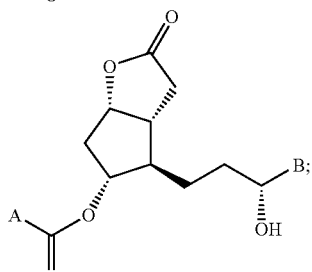

Formula (XII) includes:

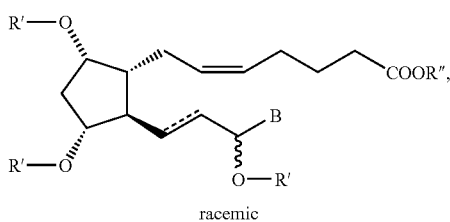

racemic

-continued

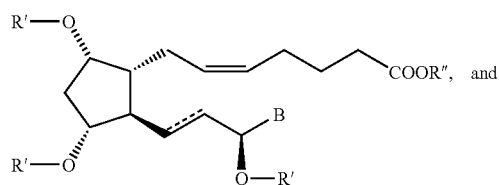

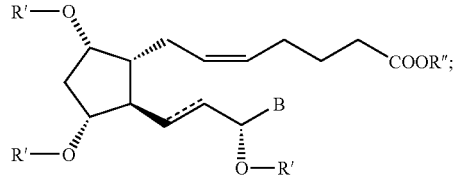

Formula (XI) includes:

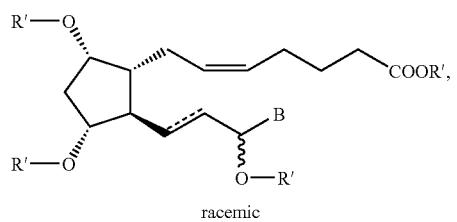

racemic

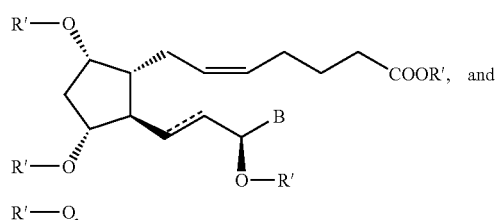

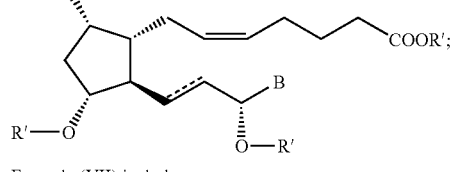

Formula (VII) includes:

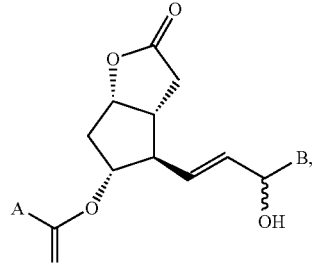

racemic

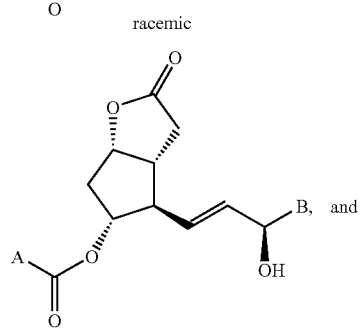

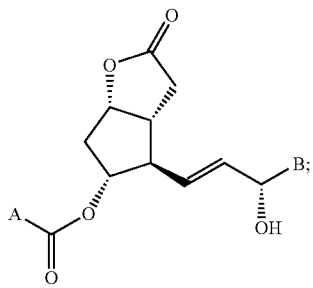
Formula (VI) includes:
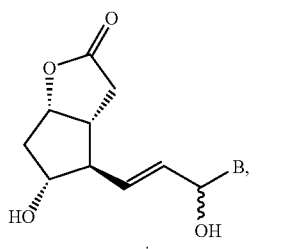
racemic
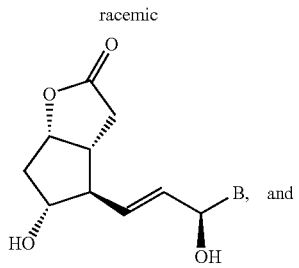
and
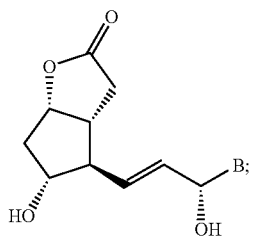
Formula (VI-A) includes:
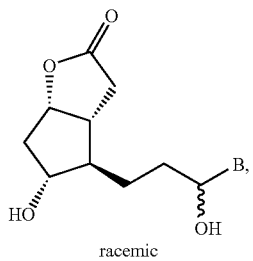
racemic
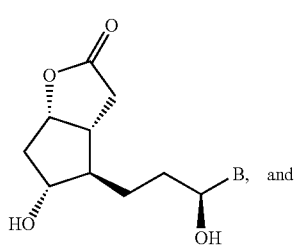
and
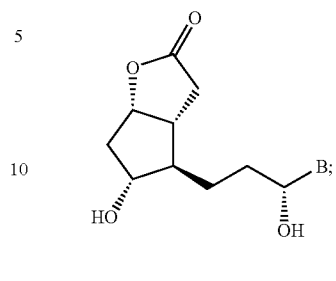
Formula (V) includes:
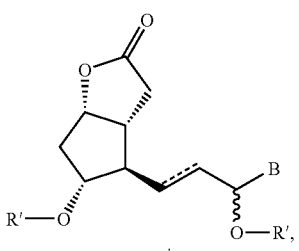
racemic
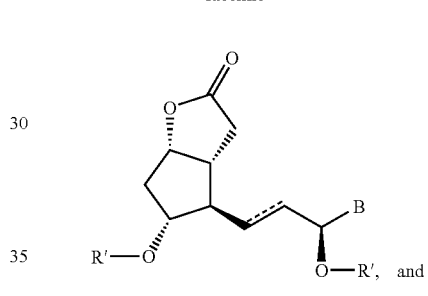
and
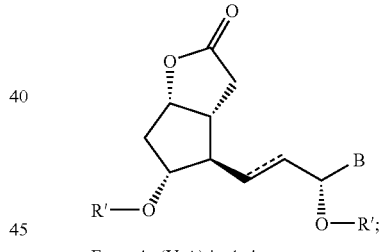
Formula (V-A) includes:
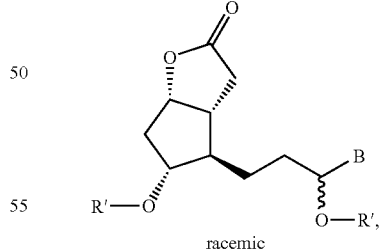
racemic
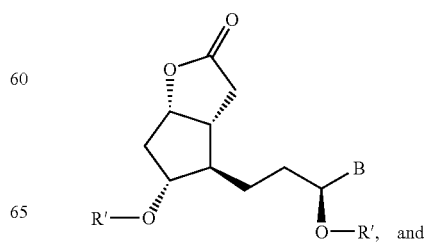
and -continued
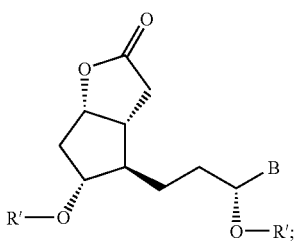
Formula (IV) includes:
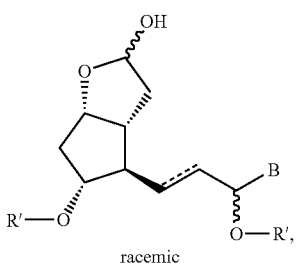
racemic
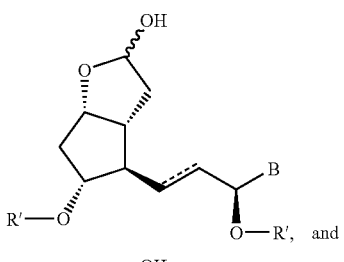
and
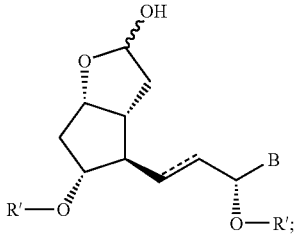
Formula (IIIa) includes:
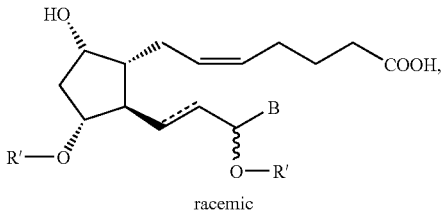
racemic
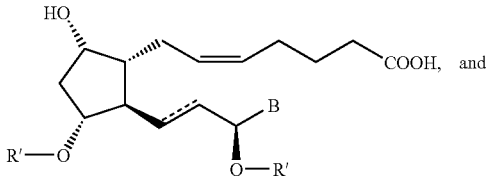
and
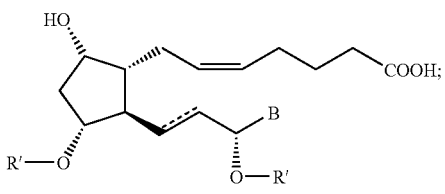
Formula (IIIb) includes:
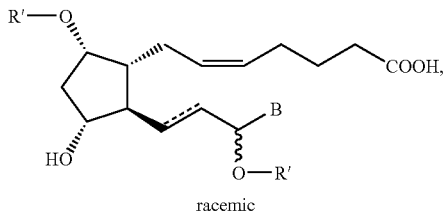
racemic
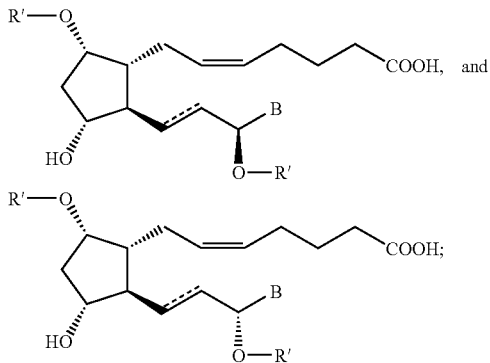
Formula (IIa) includes:
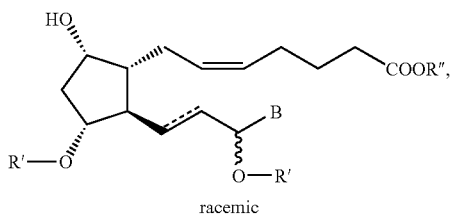
racemic
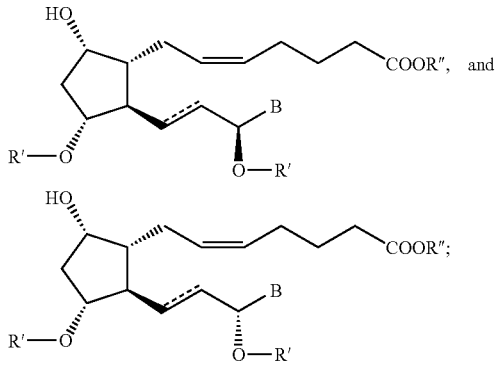
Formula (I-A) includes:
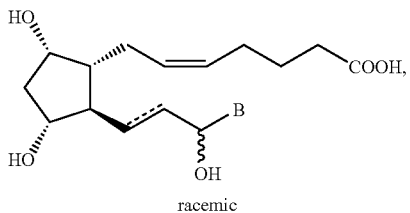
racemic -continued

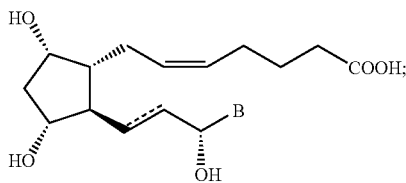

Formula (I-B) includes:

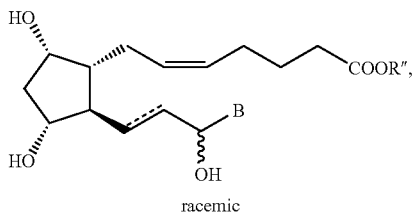
racemic

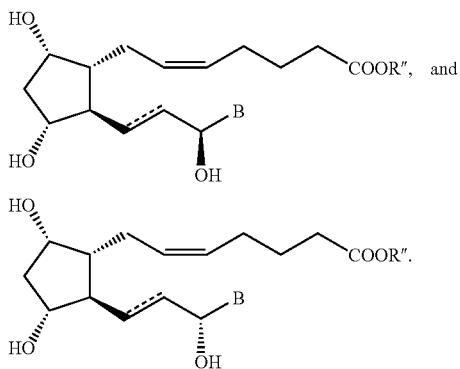

The single and dashed lines in each of the above formulae can represent optional double bonds. Thus, "-----" represents either a single bond or a double bond.

It has been found that the major impurities in latanoprost, particular when produced by the methods of the present invention, include the following:

the 15(S)-cis isomer of latanoprost:

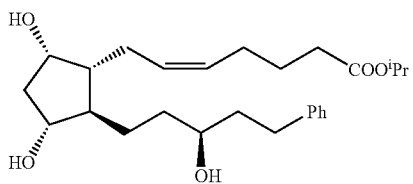

the 15(S)-trans isomer of latanoprost:

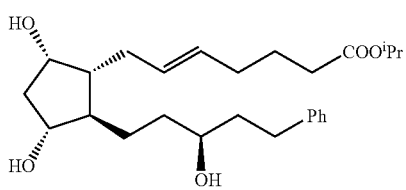

and the 15(R)-trans isomer of latanoprost:

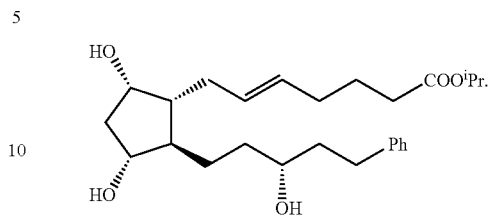

In particular, it has been found that the isomers of latanoprost are particularly difficult to remove because they have similar physical and chemical properties to latanoprost.

The present applicant has found that it is possible to obtain a separation of latanoprost from the 15(S)-cis-, 15(S)-trans- and 15(R)trans isomers of latanoprost using an HPLC purification system with a chiral column. However chiral columns are expensive and are not practical for large scale separations.

These problems have been solved by the use of a non-chiral column and a particular eluent mixture in the HPLC purification of latanoprost. Accordingly, the present invention further provides a process for the purification of latanoprost by HPLC comprising the use as an eluent, of a mixture comprising a hydrocarbon, an alcohol and, optionally, acetonitrile.

The use of such an eluent combination is a particularly preferred method of purification of latanoprost when made by the processes of the present invention. It has been found that the above eluent mixtures can achieve an extremely high purity of the latanoprost.

Preferably, the eluent comprises a hydrocarbon, an alcohol and acetonitrile. Advantageously, it has been found that the use of acetonitrile as a component of the eluent in the HPLC purification of latanoprost results in an improved separation of the impurities. In particular, the use of acetonitrile as a component of the above eluent mixture results in a significantly improved separation of the hitherto difficult to separate 15(S)-trans isomer of latanoprost. In particular, it has been found that the 15(S)-trans isomer does not co-elute with the latanoprost, i.e. a baseline separation of latanoprost of the 15(S)-trans isomer can be achieved. As a result, a higher yield of pure latanoprost may be obtained using the above eluent system compared with prior art procedures.

In particular the eluent systems in the present purification process comprises a hydrocarbon in an amount range of 80-99 volume percent and an alcohol in an amount range of 1-20 volume percent. Preferably, the eluent comprises a hydrocarbon in an amount range of 85-99 volume percent and an alcohol in an amount range of 1-15 volume percent. Even more preferred is an eluent comprising a hydrocarbon in an amount range of 88-98 volume percent and an alcohol in an amount range of 2-12 volume percent.

In the preferred acetonitrile-containing eluent systems of the present purification process, the eluent comprises a hydrocarbon in an amount range of 85-99 volume percent, an alcohol in an amount of 0.5-10 volume percent and acetonitrile in an amount of 0.5-5 volume percent. Preferred is an eluent comprises a hydrocarbon in an amount range of 86-98 volume percent, an alcohol in an amount of 1-8 volume percent and acetonitrile in an amount of 1-6 volume percent. Especially preferred is an eluent comprising a hydrocarbon in an amount range of 90-96 volume percent, an alcohol in an amount of 2-6 volume percent and acetonitrile in an amount of 2-4 volume percent.

In the above eluent systems it is preferred that the hydrocarbon is a $C_5$ to $C_8$ straight chain, branched or cyclic hydrocarbon, wherein the hydrocarbon is preferably an n-alkane. Hexane and heptane are especially preferred. The hydrocarbon employed in the eluent may comprise a mixture of e.g. alkanes, such as hexane fraction. It has been found that good results have been obtained with n-heptane.

Preferred alcohols in the above eluent systems are $C_1$ to $C_8$ straight chain, branched or cyclic alkanols, with $C_1$ to $C_5$ straight chain or branched alkanols being particularly preferred. Of these, methanol, ethanol, propan-1-ol, propan-2-ol, butan-1-ol or butan-2-ol are especially useful. Good results have been obtained with propan-2-ol (isopropanol) as the alcohol component. The use of ethanol as the alcohol component has also produced good separations. The alcohol component of the eluent can include mixtures of one or more alkanols, e.g. combinations of two or more of isopropanol, ethanol and methanol may be used, e.g mixtures in ratios of 1:1 to 3:1 have been successfully employed.

A preferred eluent system comprises n-heptane:isopropanol:acetonitrile. Preferred volume percent ranges of n-heptane:isopropanol:acetonitrile are 90-96%:2-7%:2-5%. Preferably, the ratios of n-heptane:isopropanol:acetonitrile are in the ranges 92-94%:3-5%:2-4%. Good results have been obtained with ratios of 93%:4%:3%.

The above HPLC procedures are preferably carried out on a silica gel column. Examples of suitable columns include Waters$^{RTM}$ Spherisorb, Phenomenex$^{RTM}$Luna Cyano and Phenomenex$^{RTM}$Luna Silica.

By using the above separation procedures, it has been found possible to produce latanoprost that is substantially free of the 15(S)-cis isomer, the 15(S)-trans isomer and the 15(R)-trans isomer. In particular, latanoprost containing less than 0.3% in total of any combination of. 15(S)-cis isomer, 15(S)-trans isomer and 15(R)-trans isomer may be produced. Using the process of the present invention, latanoprost containing less than 0.1% each of 15(S)-cis-, 15(S)-trans- and 15(R)-trans isomers can be produced.

The above processes thus enable latanoprost having an extremely high degree of purity can be obtained, e.g. greater than 98% pure, greater than 99% pure, greater than 99.5% pure. Indeed, it has been found possible to achieve latanoprost purities of greater than 99.8%.

The following abbreviations have been used:
HPLC=high pressure liquid chromatography
MPLC=medium pressure liquid chromatography
L-Selectride=lithium tri-sec-butylborohydride
DMS=dimethylsulfide
DIBAL-H=di-iso-butylaluminiumhydride
PPB=para-phenylbenzoyl
DBU=[1,8-diazabicyclo(5.4.0)undec-7-ene]
$^n$BuLi=n-butyllithium
TEMPO, free radical=2,2,6,6-tetramethyl-1-piperidinyloxy, free radical
EtOAc=ethylacetate
DMF=dimethylformamide TsOH=para-toluenesulphonic acid
KO$^t$Bu=potassium tert-butoxide

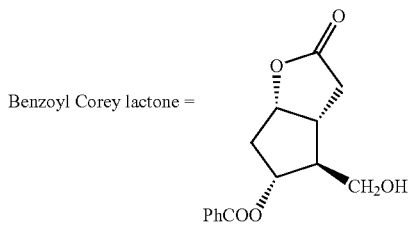

Benzoyl Corey lactone =

As used herein the term "alkyl" refers to $C_1$ to $C_6$ straight or branched carbon chains. Particularly preferred alkyl groups for the compounds and processes of the invention include methyl, ethyl, propyl, isopropyl, butyl, and tertiary butyl.

The term "aryl" represents a carbocyclic group containing from six to fifteen carbon atoms and having at least one aromatic ring. Particularly preferred aryl groups for any of the compounds and methods of the present invention include phenyl and naphthyl.

The term "aralkyl" refers to an alkyl group as defined above wherein one or more hydrogen atoms (preferably one) have been replaced by unsubstituted $C_6$ to $C_{10}$ aryl groups as defined above. A preferred aralkyl group for the compounds and methods of the invention is benzyl.

The term "halo" refers to fluoro, chloro, bromo or Iodo.

The term "substantially free" of a particular impurity refers to less than 1%, preferably less than 0.5%, more preferably, less than 0.3% and even more preferably, less than 0.1% of the impurity.

The following examples illustrates the preparation of latanoprost in accordance with the present invention:

EXAMPLES

Solvents (chromatography grade) were dried over 3 Å molecular sieves prior to use. Purified water was obtained from Loveridge.

The products obtained in the reactions were sealed under argon and stored in a cold room at 4° C. until required.

Column chromatography was carried out on Merck silica gel 60.

As a precaution, where indicated, reactions were carried out under argon. Reaction progress was monitored by thin layer chromatography.

Unless indicated otherwise, final products were dried under high vacuum at a pressure of about 0.01 kPa.

Example 1

Preparation of (1S,5R,6R,7R)-7-Benzoyloxy-6-formyl-2-oxabicyclo[3.3.0]octan-3-one (PGX-5)

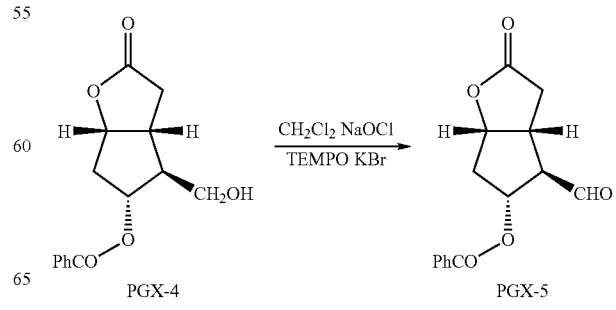

A 0.5M solution of potassium bromide was prepared by dissolving KBr (11.9 g) in purified water and then diluting with additional water to 200 ml.

2.1M Sodium hypochlorite solution (476 ml, 1M) was diluted to 1L by the addition of purified water to give a 1M solution. The pH was then adjusted to 8.83 by the addition, with stirring, of solid sodium bicarbonate.

(−)-Benzyl Corey Lactone (PGX-4) (200 g, 0.724M, 1 eq.) was dissolved in dichloromethane (2L) under an inert atmosphere and 2,2,6,6-tetramethyl-1-piperidinyloxy (TEMPO) free radical (1.13 g, 7.24 mmol, 0.01 eq.) and the aqueous potassium bromide solution prepared above added. The mixture was cooled to approximately 0° C. with stirring and a portion of the aqueous sodium hypochlorite solution prepared above (100 ml) added at this temperature. The reaction was allowed to warm to 10° C. and an additional quantity of the aqueous sodium hypochlorite solution (896 ml) added at 10-15° C. over 40 minutes. After stirring for 20 minutes the reaction was shown to be complete by TLC. The layers were separated, the aqueous phase extracted with dichloromethane (200 ml) and the combined organic phases then washed with water (200 ml) before drying over magnesium sulfate. Filtration and washing of the filtercake with dichloromethane (2×200 ml) gave (1S,5R,6R,7R)-7-benzoyloxy-6-formyl-2-oxabicyclo[3.3.0]octan-3-one (PGX-5) as a solution in dichloromethane.

Example 2

Preparation of Dimethyl2-oxo-4-phenylbutyl)-phosphonate (PGX-3)

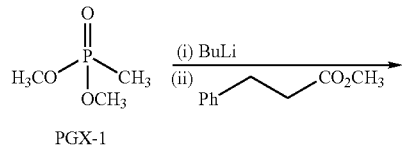

PGX-1

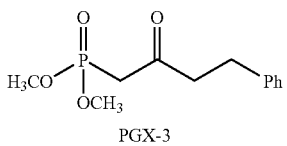

PGX-3

Dimethyl methyl phosphonate (PGX-1) (346.2 g, 2.79M, 1.95 eq.) was dissolved in tetrahydrofuran (2.4L) and the resulting solution cooled to −70° C. under an inert atmosphere. n-Butyllithium (2.5M in tetrahydrofuran, 1.0L, 2.5M, 1.75 eq.) was added over 105 minutes whilst maintaining the temperature below −65° C. The resulting white suspension was stirred at approximately −70° C. for 20 minutes. A solution of methyl 3-phenyl propionate (PGX-2) (234.8 g, 1.43M, 1.0 eq.) in tetrahydrofuran (400 ml) was then added over 30 minutes whilst maintaining the temperature below 65° C. The mixture was left to stir at approximately −70° C. for 2.5 h until the reaction was complete by TLC. After allowing to warm to approximately 0° C. the reaction was quenched by addition of water (800 ml). tert-Butylmethyl ether (1.0L) was added and the mixture allowed to separate. The organic phase was extracted with water (5×500 ml), and the combined aqueous phases acidified to pH 2 by the addition of 10% hydrochloric add (ca. 110 ml). The product was extracted into tert-butylmethyl ether (2×800 ml, then 5×500 ml) and the combined organics dried over magnesium sulfate. Filtration, washing the filtercake with tert-butylmethyl ether (400 ml) and evaporation gave the crude product as an oil (240.4 g). Distillation under reduced pressure (bp 152-156° C. at $8\times10^{-5}$-$1\times10^{-4}$ torr) gave dimethyl (2-oxo-4-phenylbutyl)phosphonate as an almost colourless oil (214.1 g 58%).

Example 3

Preparation of (1S,5R,6R,7R)-7-Benzovloxy-6-[3-oxo-5-phenyl-(E)-I-pentenyl]-2-oxabipyclo[3.3.0]octan-3-one (PGX-6)

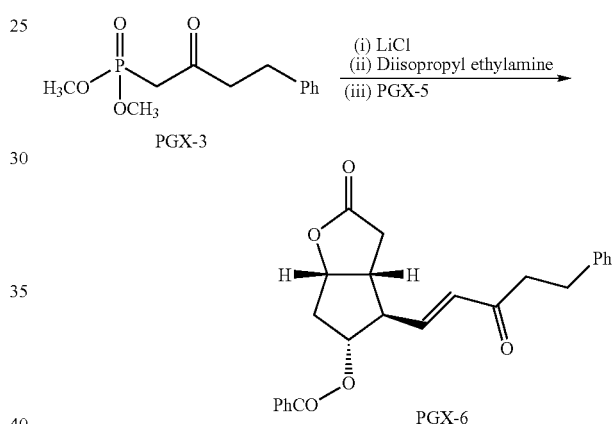

The phosphonate ester (PGX-3) (176.2 g, 0.69M, 0.95 eq.) was dissolved In dry acetonitrile (1.8L) in an inert atmosphere and lithium chloride (153.4 g, 3.62M, 5.0 eq.) added. The mixture was cooled to approximately −15° C. and dry diisopropyl ethylamine (178.1 g, 1.38M, 1.9 eq.) added over 10 minutes whilst maintaining this temperature. After stirring for about 100 minutes a solution of the aldehyde (PGX-5) in dry dichloromethane (from Step 2) (assumed 0.72M, 1.0 eq.) was added over 20 minutes whilst maintaining the temperature at ca. −15° C. The reaction was then allowed to warm to ambient temperature with stirring until TLC showed it was complete. Water (200 ml) was added and the mixture evaporated in vacuo to remove the majority of the acetonitrile. The residual slurry was partitioned between water (2.0L) and ethyl acetate (2.0L). The organic phase was separated off and the aqueous extracted with ethyl acetate (2×500 ml). The combined organics were washed with saturated brine (2×1L) and dried over magnesium sulfate. After filtration, the solvent was evaporated off to a residual weight of ca. 540 g and hexane (1L) then added to the residue. After cooling to 4° C. with stirring for 90 minutes the solid was filtered off, washed with hexane:ethyl acetate 4:1 (2×200 ml) and dried in vacuo at ambient temperature to give (1S,5R,6R,7R)-7-benzoyloxy-6-[3-oxo-5-phenyl-(E)-1-pentenyl]-2-oxabicyclo[3.3.0]octan-3-one as a white solid (225.8 g, 77%).

Example 4

Preparation of (R)-Tetrahydro-1-methyl-3,3-diphenyl-1H,3H-pyrrolo [1,2-c][1,3,2]oxazaborole (Corey Catalyst)

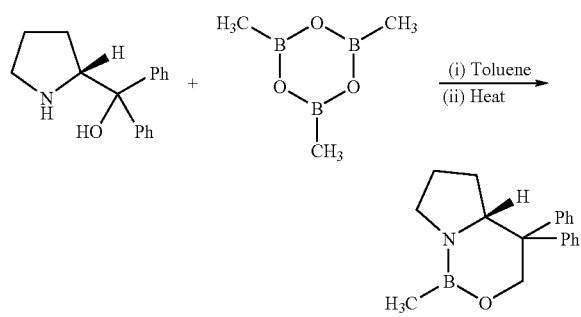

(R)-(+), 1,1-Diphenylprolinol (15.20 g, 60.0 mMol) was dissolved in toluene (600 ml) under an inert atmosphere and trimethylboroxine (7.57 g, 60.3 mMol, 1.0 eq.) added. The mixture was heated to reflux and approximately half of the toluene was distilled off via a Dean-Stark trap. Further toluene (350 ml) was added and this was also distilled off via the Dean-Stark trap until a total of 710 ml of distillate had been collected. The reaction mixture was then allowed to cool to ambient temperature to give (R)-tetrahydro-1-methyl-3,3-diphenyl-1H,3H-pyrrolo[1,2-c][1,3,2]oxazaborole as a 0.25M solution in toluene.

Example 5

Preparation of (1S,5R,6R,7R)-7-Benzoyloxy-6-[3 (S)-3-hydroxy-5-phenyl-1(E)-pentenyl]-2-oxabicyclo [3.3.0]octan-3-one (PGX-7)

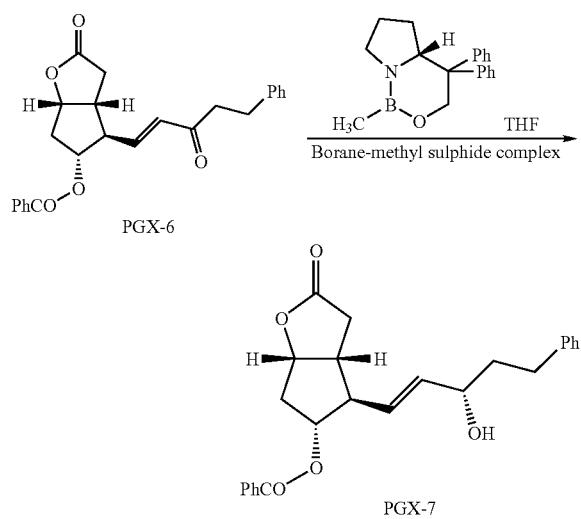

PGX-6 (225.1 g, 0.556M) was dissolved in dry tetrahydrofuran (3.5L) in an inert atmosphere and 'Corey catalyst' prepared according to Example 4 (0.25M in toluene, 223 ml, 0.1 eq.) added. The mixture was cooled to approximately −15° C. and a solution of borane-methyl sulfide complex (10M BH$_3$ concentration, 41.7 ml, 417 mMol, 0.75 eq.) in dry tetrahydrofuran (450 ml) was added whilst maintaining the temperature at ca. 15° C. The mixture was then stirred at this temperature for 2 h until the reaction was shown to be complete by TLC. Methanol (200 ml) was added over 30 minutes and the mixture allowed to warm to approximately 0° C. before acidification with 10% aqueous hydrochloric acid (1.2L): Ethyl acetate (2.4L) was added and the layers allowed to separate. The aqueous phase was extracted with ethyl acetate (1×0.8L, 1×0.4L) and the combined organic phases washed with water (1×1.6L, 3×0.8L) and then brine (1L). Drying over magnesium sulfate, filtration and evaporation in vacuo gave the crude product (containing a mixture of the desired 3(S)-isomer, PGX-7, and the undesired 3(R)-isomer PGX-8) as an oil (242.7 g). This was dissolved in dichloromethane:ethyl acetate 2:1 (720 ml) and chromatographed on silica gel 60 (12.8 Kg) eluting with dichloromethane:ethyl acetate 2:1. Impure fractions containing a mixture of PGX-7 and PGX-8 were evaporated and re-chromatographed under the same conditions. Fractions free from PGX-8 (by TLC) were combined and evaporated. Drying in vacuo at ambient temperature gave the desired product (1S,5R,6R,7R)-7-benzoyloxy-6-[3(S)-3-hydroxy-5-phenyl-1(E)-pentenyl]-2-oxa-bicyclo [3.3.0]octan-3-one as a white solid (167.9 g, 74.2%).

Example 5a

Preparation of (1S,5R,6R,7R)-7-Benzoyloxy-6-[3 (S)-3-hydroxy-5-phenyl-1 (E)-pentenyl]-2-oxabicyclo[3.3.0]octan-3-one (PGX 7)

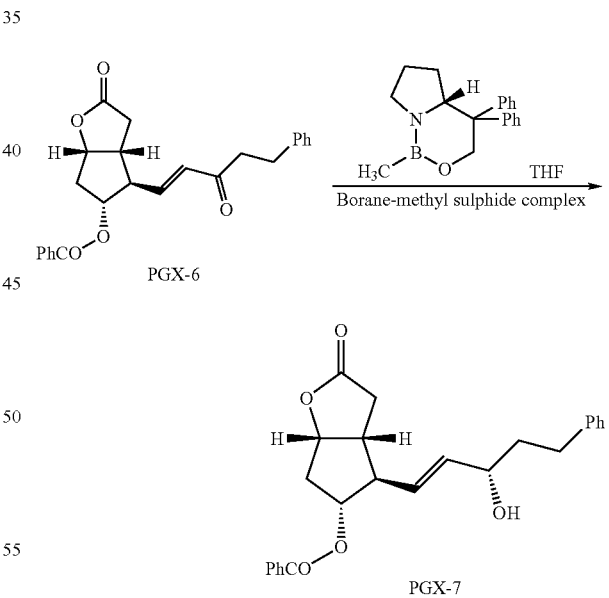

PGX 6 (315.2 g, 0.779M) was dissolved in dry tetrahydrofuran (5.7L) in an inert atmosphere and 'Corey catalyst' (0.25M in toluene, 312 ml, 0.1 eq.) added. The mixture was cooled to approximately −15° C. and a solution of borane-methyl sulfide complex (10M BH$_3$ concentration, 58.5 ml, 0.585M, 0.75 eq.) in dry tetrahydrofuran (630 mL) added whilst maintaining the temperature at ca. 15° C. The mixture was then stirred at this temperature for 2 h until the reaction was shown to be complete by TLC. Methanol (290 ml) was added over 30 minutes and the mixture allowed to warm to approximately 0° C. before acidification with 10% aqueous hydrochloric acid (1.7L). Ethyl acetate (3L), was added and the layers allowed to separate. The aqueous phase was extracted with ethyl acetate (1×1.1L, 1×0.55L) and the combined organic phases washed with water (1×2L, 3×1L) and then brine (1.5L). Drying over magnesium sulfate, filtration and evaporation in vacuo gave the crude product (containing a mixture of PGX 7 and the undesired isomer PGX 8) as an oil (349.3 g). The oil was purified by the procedure given in Example 5b.

Note:

The chromatographic procedure described in Example 5 in which a 2:1 mixture of dichloromethane:ethylacetate is employed as an eluent for medium pressure chromatography (MPLC) on a silica gel column, suffers from the disadvantage that the column must be re-packed after each separation before subsequent aliquots of the epimeric product mixture can be processed. Thus, such a procedure employs large quantities of both stationary phase and eluent, as well as being time consuming. An improved procedure is given below (Example 5b):

Example 5b

Separation of (1S,5R,6R,7R)-7-Benzoyloxy-6-[3(S)-3-hydroxy-5-phenyl-1(E)-pentenyl]-2-oxabicyclo[3.3.0]octant-one (PGX-7) from (1S,5R,6R,7R)-7-Benzoyloxy-6-[3(R)-3-hydroxy-5-phenyl-1 (E)-pentenyl]-2-oxabicyclo[3.3.0]octan-3-one (PGX-8)

According to an improved procedure, the crude mixture of epimers PGX-7/PGX-8 (686.5 g) made according to the synthetic procedure described in Example 5a was crystallised from heptane fraction/ethyl acetate (7:3) to give a crystalline mixture of epimers PGX-7 and PGX-8 (480.4 g) that is free of other impurities. The filtrates from the crystallisation were evaporated to give an oil (150.3 g) comprising mainly impure PGX-7/PGX-8.

The crystalline mixture was dissolved in dichloromethane:ethyl acetate (2:1) mixture to give a stock solution (A). The evaporated impure PGX-7/PGX-8 mixture was dissolved in dichloromethane:ethyl acetate (2:1) mixture to give a second stock solution (B). The isomer PGX-7 was then separated from PGX-8 by medium pressure chromatography (MPLC) on a silica gel column by sequential injection of aliquots of the stock solutions according to the following protocol:

Injection 1: Injection of an aliquot of crystalline PGX-7/PGX-8 stock solution (A) and collection of appropriate fractions containing pure PGX-7 and impure PGX-7. The column was then flushed with eluent to elute any remaining PGX-8.

Injection 2: Injection of an aliquot of crystalline PGX-7/PGX-8 stock solution (A) and collection of appropriate fractions containing pure PGX-7 and impure PGX-7. Column flushed with methanol then equilibration of column with eluent.

Injection 3: Injection of an aliquot of impure PGX-7/PGX-8 stock solution (B) and collection of appropriate fractions containing pure PGX-7 and impure PGX-7 and impure PGX-7. Discarded silica gel and re-packed column with fresh silica gel and repeat cycle.

The above strategy increases the throughput of PGX-7 considerably and avoids the need to re-pack the column after every injection.

The column fractions containing the impure PGX-7 are recycled to give more pure PGX-7 utilising the above protocol, except that more than three injections per column can be performed before re-packing the column.

Fractions free from PGX-8 (by TLC) were combined and evaporated. Drying in vacuo at ambient temperature gave (1S,5R,6R,7R)-7-benzoyloxy-6-[3(S)-3-hydroxy-5-phenyl-1(E)-pentenyl]-2-oxabicyclo[3.3.0]octan-3-one (PGX-7) as a white solid (445.2 g).

Example 6

Preparation of (1S,5R,6R,7R)-7-Hydroxy-6-[3(S)-3-hydroxy-5-phenyl-1 (E)-pentenyl]-2-oxabicyclo[3.3.0]octan-3-one (PGX-9)

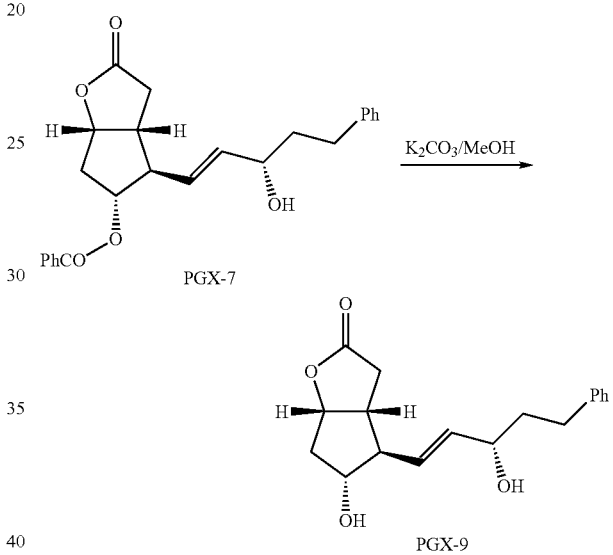

PGX-7 (152.0 g, 0.374M, 1.0 eq.) was dissolved in dry methanol (2.28L) under an inert atmosphere and potassium carbonate (31.0 g, 0.224M, 0.6 eq.) added in one portion. The mixture was stirred at ambient temperature for 3 h until TLC showed the reaction was complete. 5M Hydrochloric acid (65.5 ml) was added to adjust the apparent pH of the solution to about 6.8-7.0 and the mixture then evaporated to dryness in vacuo. The sticky residue was treated with water (1.5L) and the pH adjusted to 6.8-7.0 by the addition of 1M hydrochloric acid (7 ml). Heptane (0.45L) was added, the mixture agitated vigorously and the precipitated solid filtered off and washed with heptane (2×150 ml) on the filter. The solid was then triturated with a further quantity of heptane (2×150 ml). All the heptane washes were combined and added to the original filtrates. The aqueous phase was separated off, washed with heptane (2×150 ml) and then extracted with ethyl acetate (1×450 ml, 3×150 ml). The previously isolated solid was added to the combined ethyl acetate extracts and the mixture shaken until a solution formed. This was washed with saturated brine (2×250 ml) and dried over magnesium sulfate. Filtration and evaporation in vacuo gave (1S,5R,6R,7R)-7-hydroxy-6-[3(S)-3-hydroxy-5-phenyl-1(E)-pentenyl]-2-oxabicyclo[3.3.0]octan-3-one as a pale yellow oil (112.1 g, 99.1%).

Example 7

Preparation of (1S,5R,6R,7R)-7-Hydroxy-6-[3(R)-(3-hydroxy-5-phenyl)pentyl]-2-oxabicyclo[3.3.0]octan-3-one (PGX-10)

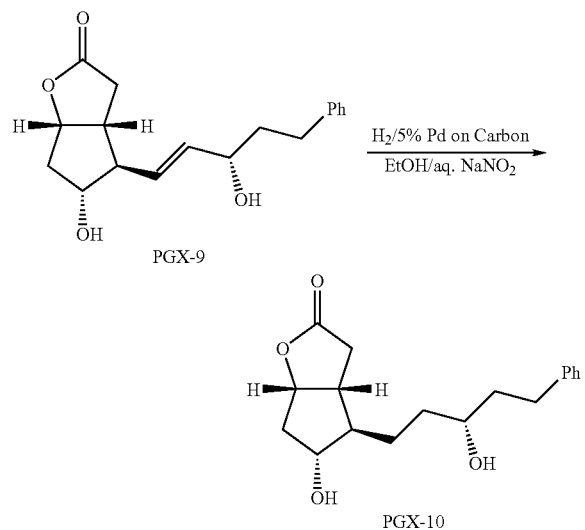

Example 7a

Preparation of (1S,5R,6R,7R)-7-Hydroxy-6-[3(R)-(3-hydroxy-5-phenyl)pentyl]-2-oxabicyclo[3.3.0]octan-3-one (PGX 10)

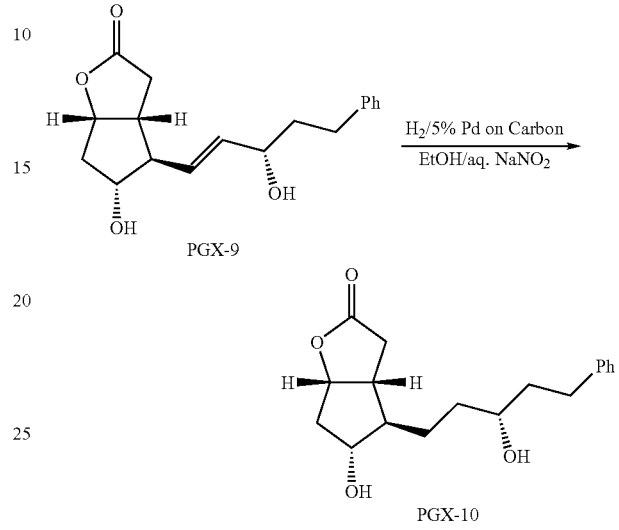

PGX-9 (111.5 g 0.369M, 1.0 eq.) was dissolved in ethanol (1.67L) and 5% palladium on carbon (5.58 g) added followed by a solution of sodium nitrite (8.90 g, 0.129M, 0.35 eq.) in water (100 ml). The mixture was then hydrogenated for 5 h until shown to be complete by TLC. 1M Hydrochloric acid (260 ml) was added and the mixture stirred for 1 h. The solids were removed by filtration through celite, the filtrates then evaporated to give an oily-solid residue which was partitioned between ethyl acetate (0.45L) and water (0.45L). The layers were separated and the aqueous extracted with ethyl acetate (2×0.33L). The combined organics were washed with brine (2×0.22L) and then dried over sodium sulfate containing 5% sodium hydrogen carbonate. Filtration and evaporation gave (1S, 5R, 6R, 7R)-7-Hydroxy-6-[3(R)-(3-hydroxy-5-phenyl)pentyl]-2-oxabicyclo[3.3.0]octan-3-one as a yellow oil (110.4 g, 98.4%)

Note:

It has been found to be possible to reduce the time period during which the product PGX-10 is in the acid medium during the HCl work-up, and thus minimise the potential of an acid-catalysed epimerisation of the side-chain hydroxyl group of (1S,5R,6R,7R-7-Hydroxy-6-[3(R)-(3-hydroxy-5-phenyl)-pentyl]-2-oxabicyclo[3.3.0]octan-3-one Thus, in the modified procedure, on completion of the reaction described in Example 7, 1M hydrochloric acid was added and the reaction mixture stirred for 60 minutes as described in Example 7. The pH of the mixture was adjusted to between 5 and 6 by addition of solid sodium hydrogen carbonate prior to the filtration of the used catalyst, and evaporation of the filtrate to dryness. The work-up is then completed as described in Example 7 by extraction of the product into ethyl acetate. The following Example 7a illustrates the improved procedure:

PGX 9 (326.5 g, 1.08M, 1.0 eq.) was dissolved in ethanol (6.5L) and 5% palladium on carbon (16.3 g) added followed by a solution of sodium nitrite (26 g, 0.377M, 0.35 eq.) in water (200 ml). The mixture was then hydrogenated for 1.5 h until shown to be complete by TLC. 1M Hydrochloric acid (750 ml) was added and the mixture stirred for 1 h. The pH was adjusted to 5-6 by the addition of solid sodium hydrogen carbonate (55 g). The solids were removed by filtration through celite, the filtrates then evaporated to give an oily-solid residue which was partitioned between ethyl acetate (1.3L) and water (1.3L). The layers were separated and the aqueous extracted with ethyl acetate (2×0.975L). The combined organics were washed with brine (2×0.65L) and then dried over sodium sulfate. Filtration and evaporation gave (1S,5R,6R,7R)-7-Hydroxy-6-[3(R-(3-hydroxy-5-phenyl)pentyl]-2-oxabicyclo[3.3.0]octan-3-one as a yellow oil (311.5 g, 94.8%).

Example 8

Preparation of (1S,5R,6R,7R)-6-[3(R)-(5-phenyl-3-triethyl silyloxy)pentyl]-7-triethylsilyloxy-2-oxabicyclo[3.3.0]octan-3-one (PGX-11)

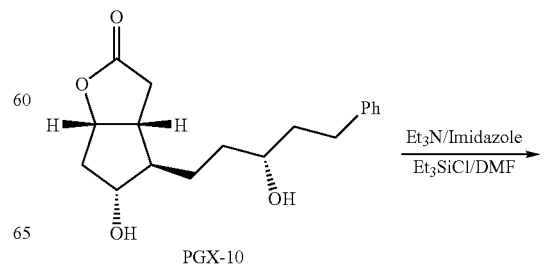

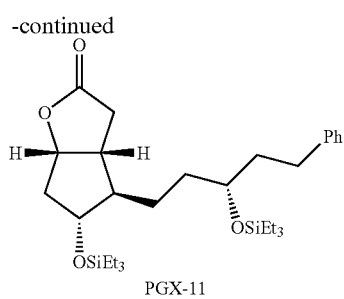

PGX-10 (109.7 g, 0.360M, 1.0 eq.) was dissolved in dry dimethyl formamide (720 ml) under an inert atmosphere. Imidazole (29.4 g, 0.432M, 1.2 eq.) and triethylamine (102.9 ml, 74.69 g, 0.738M, 2.05 eq.) were added and the mixture then cooled to approximately 0° C. Triethylchlorosilane (111.2 g, 0.738M, 2.05 eq.) was added over 15 minutes at less than 10° C. The mixture was allowed to warm to room temperature and stirred for 2 h until TLC showed the reaction was complete. After re-cooling to 10° C., hexane (0.55L) and water (1L) were added and the layers separated. The aqueous phase was extracted with hexane (1×0.2L, 1×0.1L) and the combined organics then washed with water (2×0.5L) and brine (2×0.5L). Drying over magnesium sulfate, filtration and evaporation in vacuo gave (1S,5R,6R,7R)-6-[3(R)-(5-phenyl-3-triethylsilyloxy)pentyl]-7-triethylsilyloxy-2-oxabicyclo[3.3.0]octan-3-one as a yellow oil (187.4 g, 97.6%).

Example 9

Preparation of (1S,3RS,5R,6R,7R)-6-[3(R)-(5-phenyl-3-triethylsilyloxy)pentyl]-7-triethylsilyloxy-2-oxabicyclo[3.3.0]octan-3-ol (PGX-12)

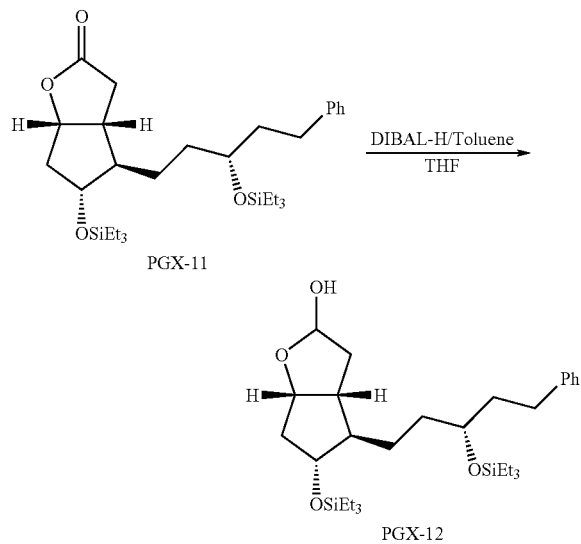

PGX-11 (186.8 g, 0.3505M, 1.0 eq.) was dissolved in dry tetrahydrofuran (1.86L) under an inert atmosphere and the solution cooled to less than −70° C. Diisobutylaluminium hydride (1.1M in toluene solution, 701 ml, 0.7711M, 2.2 eq.) was added to the reaction whilst maintaining the temperature below −70° C. The mixture was then stirred at this temperature for 2 h until the reaction was shown to be complete by TLC. Methanol (132 ml) was added and the mixture allowed to warm to −5° C. before addition of water (2L) followed by acidification to pH 3 with 2M aqueous sodium hydrogen sulphate solution is (1.54L, 8.8 eq.). Ethyl acetate (0.66L) was added and the layers allowed to separate. The aqueous phase was extracted with ethyl acetate (1×0.26L, 1×0.13L) and the combined organics then washed with water (2×1.3L) and brine (2×1.3L). Drying over magnesium sulfate and evaporation in vacuo gave (1S,3RS,5R,6R,7R)-6-[3(R)-(5-phenyl-3-triethylsilyloxy)pentyl]-7-triethyl-silyloxy-2-oxabicyclo[3.3.0]octan-3-ol as an almost colourless oil (182.5 g).

Example 10

Preparation of (Z)-7-{(1R,2R,3R,5S)-5-Hydroxy-2-[3(R)-(5-phenyl-3-triethylsilyloxy)pentyl]-3-(triethylsilyloxy)cyclopentyl}-5-heptenoic acid (PGX-13) and (Z)-7-{(1R,2R,3R,5S)-3-Hydroxy-2-[3(R)-(5-phenyl-3-triethyl-silyloxy)pentyl]-5-(triethylsilyloxy)cyclopentyl}-5-heptenoic acid (PGX-14)

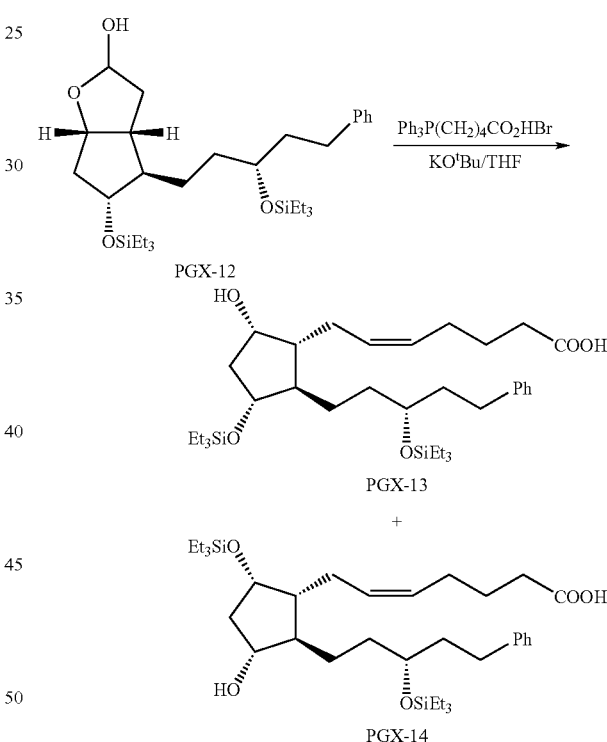

(4-Carboxybutyl)-trphenylphosphonium bromide (459.0 g, 1.0353M, 3.0 eq.) was suspended in dry tetrahydrofuran (1.84L) under an inert atmosphere and the mixture cooled to 0° C. 1.07M Potassium tert-butoxide in tetrahydrofuran solution (1.806L, 1.93M, 5.6 eq.) was then added over 60 minutes at 0° C. After the addition was complete the reaction was allowed to warm to approximately 20° C. and stirred for 1 hour before re-cooling to 0° C. A solution is of PGX-12 (184.6 g, 0.3451M, 1.0 eq.) in tetrahydrofuran (0.27L) was then added at this temperature. The mixture was allowed to warm to room temperature and stirred for 75 minutes until TLC showed the reaction was complete. After re-cooling to 0° C. the mixture was quenched by the addition of water (3L) and then acidified to pH 5 with 5% aqueous citric acid solution (1.6L). The product was extracted into ethyl acetate (1×1.0L, 2×0.4L) and the combined organics then washed with brine (2×0.7L). Drying over magnesium sulfate, filtration and evaporation in vacuo gave a mixture of (Z)-7-(1R,2R,3R,5S)-5-hydroxy-2-[3(R)-(5-phenyl-3-triethylsilyloxy) pentyl]-3-(triethylsilyloxy) cyclo-pentyl)₅-heptenoic acid and (Z)-7-{(1R,2R,3R,5S)-3-hydroxy-2-[3(R)-(5-phenyl-3-triethyl-silyloxy) pentyl]-5-(triethylsilyloxy)cyclo-pentyl}-5-heptenoic acid as a yellow oil (461.7 g). This crude product containing triphenylphosphine oxide by-product was used without purification in the next step of the synthesis.

Note:

The amount of (4-carboxybutyl)triphenylphosphonium bromide used in the above reaction is 3.0 equivalents with respect to the amount of starting material PGX-12 used. In order to generate the ylide and the carboxylate salt, it is treated with 5.6 equivalents of potassium tert-butoxide. The slight deficit in the amount of potassium tert-butoxide used with respect to (4-carboxybutyl)triphenylphosphonium bromide (2.0 equivalents required; 1.87 equivalents used) is deliberate to ensure that all of the potassium tert-butoxide is consumed and is not present during the reaction with the lactol.

However, the present applicant has found that 2.15 equivalents of (4-carboxybutyl)triphenylphosphonium bromide and 4.0 equivalents of potassium tert-butoxide with respect to the amount of the lactol starting material PGX-12 can be used. Advantageously, this leads to a better conversion of PGX-12 to PGX-13/PGX-14. This is illustrated in Example 10a:

Example 10a

Preparation of (Z)-7-{(1R,2R,3R,5S)-5-Hydroxy-2-[3(R)-(5-phenyl-3-triethylsilyloxy)pentyl]-3-(triethylsilyloxy)cyclopentyl}-5-hept-enoic acid (PGX-13) and (Z)-7-{(1R,2R,3R,5S)-3-Hydroxy-2-[3(R)-(5-phenyl-3-triethyl-silyloxy)pentyl]-5-(triethylsilyloxy)cyclopentyl}-5-hept-enoic acid (PGX-14)

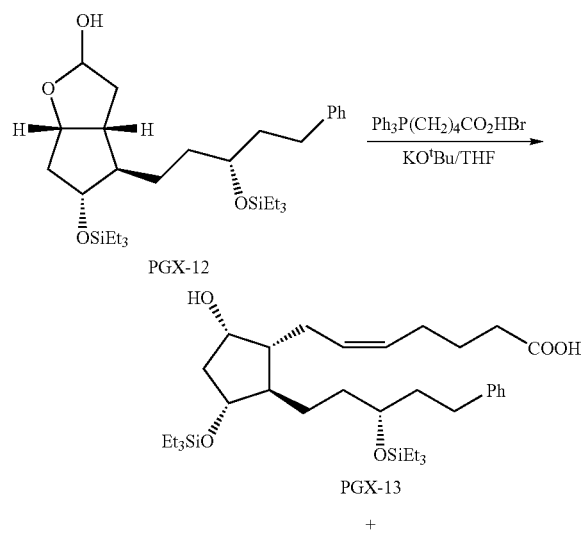

(4-Carboxybutyl)-triphenylphosphonium bromide (965.5 g, 2.18M, 2.15 eq.) was suspended in dry tetrahydrofuran (4.4L) under an inert atmosphere and the mixture cooled to 0° C. 0.98M Potassium tert-butoxide in tetrahydrofuran solution (4.135L, 4.05M, 4.0 eq.) was then added over 60 minutes at 0° C. After the addition was complete the reaction was allowed to warm to approximately 20° C. and stirred for 1 hour before re-cooling to 0° C. A solution of PGX-12 (542.3 g, 1.013M, 1.0 eq.) in tetrahydrofuran (1L) was then added at this temperature. The mixture was allowed to warm to room temperature and stirred for 60 minutes until TLC showed the reaction was complete. After re-cooling to 0° C. the mixture was quenched by the addition of water (8.6L) and then acidified to pH 5 with 5% aqueous citric acid solution (4.5L). The product was extracted into ethyl acetate (1×3L, 2×1.2L) and the combined organics then washed with brine (2×2L). Drying over magnesium sulfate, filtration and evaporation in vacuo gave a mixture of (Z)-7-{(1R, 2R, 3R, 5S)-5-hydroxy-2-[3(R)-(5-phenyl-3-triethylsilyloxy)pentyl]-3-(triethylsilyloxy) cyclopentyl}-5-heptenoic acid and (Z)7-{(1R,2R,3R,5S)-3-hydroxy-2-[3(R)-(5-phenyl-3-triethyl-silyloxy) pentyl]-5-(triethylsilyloxy)cyclo-pentyl)₅-heptenoic acid as a yellow oil (1095.6 g). This crude product containing triphenylphosphine oxide by-product was used without purification in the next step of the synthesis.

Example 11

Preparation of Isopropyl (Z)-7-{(1R,2R,3R,5S)-5-Hydroxy-2-[3(R)-(5-phenyl-3-triethylsilyloxy)pentyl]-3-(triethylsilyloxy)-cyclo-pentyl}5-heptenoate (PGX-15) and Isopropyl (Z)-74(1R,2R,3R,5S)-3-Hydroxy-2-[3(R)-(5-phenyl-3-triethylsilyloxy)pentyl]-5-(triethylsilyloxy)cyclopentyl}-5-heptenoate (PGX-16)

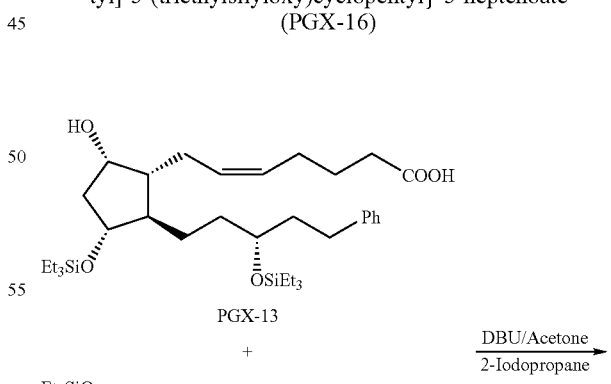

-continued

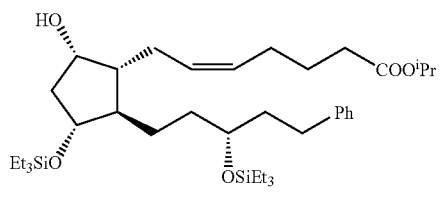

PGX-15

+

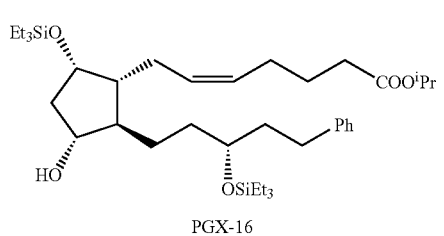

PGX-16

The PGX-13/14 mixture (461.1 g, assumed to contain 0.3446M, 1.0 eq.) was dissolved in acetone (2.13L) under an inert atmosphere and dry 1,8-diazabicyclo[5.4.0]undec-7-ene (DBU) (290.1 ml, 1.94M, 5.63 eq.) added at ambient temperature. After stirring for approximately 15 minutes, 2-iodopropane (329.7 g, 1.94M, 5.63 eq.) was added and the mixture then stirred for 16 h at ambient temperature. TLC showed that the reaction was incomplete. An additional quantity of DBU (19.1 ml, 0.1275M, 0.37 eq.) was added followed, after 20 minutes, by 2-iodopropane (21.7 g, 0.1275M, 0.37 eq.). After stirring for 4.5 h at ambient temperature the reaction was shown to be complete by TLC. The bulk of the acetone (ca. 1.72L) was evaporated in vacuo and the residue partitioned between ethyl acetate (0-67L) and 3% aqueous citric acid solution (1.6L). The organic layer was separated off and the aqueous layer acidified to pH 6 with an additional quantity of 3% aqueous citric acid solution (0.72L) and then re-extracted with ethyl acetate (2×0.33L). The combined organic phases were washed with 3% aqueous citric acid solution (2×0.8L), 5% sodium hydrogen carbonate solution (2×0.8L) and saturated brine (2×1.6L). After drying over magnesium sulfate followed by filtration the solvent was evaporated off and heptane (1.0L) and ethyl acetate (80 ml) added to the residue. The mixture was cooled to −20° C. and agitated vigorously. After 30 minutes at −20° C. the precipitated solid was filtered off and washed on the filter with heptane: ethyl acetate 9:1 (6×200 ml). Evaporation of the filtrates in vacuo gave a yellow oil. Heptane (600 ml) was added and the solution cooled to −20° C. After 30 minutes the precipitate was filtered off and washed on the filter with heptane (3×100 ml). The filtrate was evaporated in vacuo to give a mixture of isopropyl (Z-7-{(1R,2R,3R,5S)-5-hydroxy-2-[3(R)-(5-phenyl-3-triethylsilyloxy)pentyl]-3-(tri-ethylsilyloxy)cyclopentyl}-5-heptenoate and isopropyl (Z)-7-{(1R,2R,3R,5S-3-hydroxy-2-[3(R)-(5-phenyl-3-triethylsilyloxy)pentyl]-5-(tri-ethylsilyloxy)cyclo-pentyl)}-5-heptenoate as a yellow oil (238.4 g).

Example 12

Preparation of Isopropyl (Z)-7-{(1R,2R,3R,5S)-3,5-bis(triethylsilyloxy)-2-[3(R)-(5-phenyl-3-triethylsilyloxy)pentyl]-cyclo-pentyl}-5-heptenoate (PGX-17)

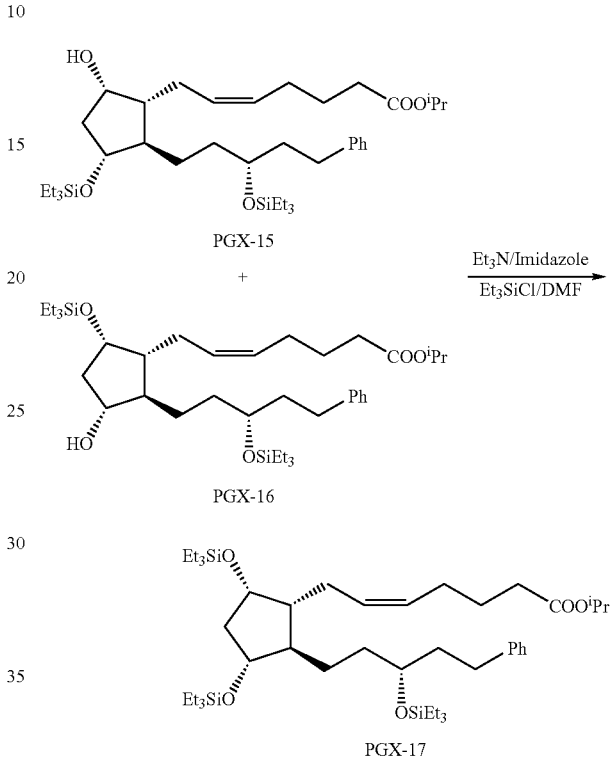

The PGX-15/16 mixture (237.79 g, assumed to contain 0.344M) was dissolved in dry dimethylformamide (700 ml) under an inert atmosphere. Imidazole (14.04 g, 0.206M, 0.6 eq.) and triethylamine (50.3 ml, 0.361M, 1.05 eq.) were added and the mixture cooled to approximately 0° C. Triethylchlorosilane (60.6 ml, 54.4 g, 0.361M, 1.05 eq.) was then added and the mixture allowed to warm to ambient temperature. Stirring was continued for 2 h until the reaction was shown to be complete by TLC. The reaction mixture was then partitioned between heptane (1.07L) and water (2.67L). After separation, the aqueous phase was further extracted with heptane (2×0.27L). The combined organics were washed with water (2×1.3L) and then saturated brine (2×1.3L). After drying over magnesium sulfate followed by filtration the solvent was evaporated in vacuo to give the crude product (235.0 g) as a thick yellow oil. This was dissolved in heptane (90 ml) and purified by column chromatography on silica gel (352.5 g) eluting with heptane and then heptane: ethyl acetate 95:5. The relevant fractions were combined and the solvent evaporated in vacuo to give isopropyl (Z)-7-{(1R,2R,3R,5S)-3,5-bis(triethylsilyloxy)-2-[3(R-(5-phenyl-3-triethylsilyloxy) pentyl] cyclopentyl}-5-heptenoate as a pale yellow oil (210.5 g).

Example 13

Preparation of Isopropyl (Z)-7-{(1R,2R,3R,5S)-3,5-dihydroxy-2-[3(R)-(3-hydroxy-5-phenyl)pentyl]cyclopentyl}-5-heptenoate (Latanoprost)

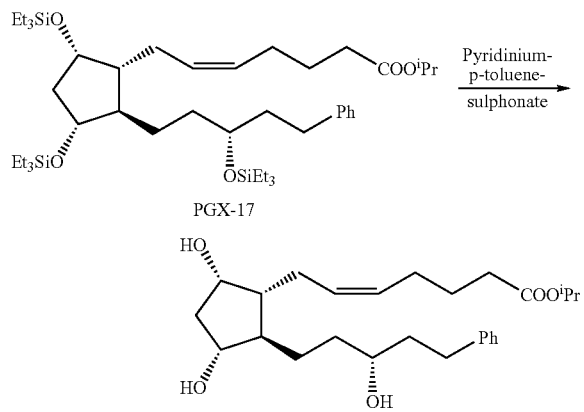

PGX-17 (0.504 g, 0.65 mmol) was weighed into a 50 ml round bottom flask equipped with a magnetic follower. Acetone (6.5 ml) was added and the resulting colourless solution stored at room temperature under a gentle stream of argon.

A solution of pyridinium-p-toluenesulfonate (Aldrich, 13 mg) in water (0.9 ml) was prepared and added to the reaction solution. The resulting white cloudy suspension was stored at room temperature under a stream of argon. The is mixture cleared after about 20 min to give a colourless solution. TLC after 3 hr indicated complete conversion to the required product. The stirring was then stopped and the reaction mixture concentrated under reduced pressure to remove the acetone. The residue was partitioned between ethylacetate (10 ml) and saturated NaCl (15 ml). The organic phase was separated and the aqueous layer extracted with more ethylacetate (2×7.5 ml). The combined organic extracts were washed with saturated NaCl (2×10 ml), dried over $MgSO_4$ (0.5 g) and evaporated to dryness under reduced pressure. The crude product was obtained as a colourless oil.

The crude product was purified by flash column chromatography. A flash column was prepared using silica gel 60 (6 g) and hexane fraction/EtOAc (1:1) as the eluent. The crude product (7 mg was removed as retention sample) was dissolved in the eluent (2 ml) and loaded onto the column. The column was then eluted with hexane fraction/EtOAc mixtures as follows:

| Hexane fraction/EtOAc | 1:1 | 50 ml |
|---|---|---|
| | 1:2 | 150 ml |
| | 1:3 | 80 ml |

The fractions containing the pure product were combined and evaporated to dryness under reduced pressure. The pure product was obtained as a colourless viscous oil which was dried under high vacuum (0.01 kPa) to constant weight (0.251 g, yield 89.3%).

Example 13a

Preparation of Isopropyl (Z)-7-{(1R,2R,3R,5S)-3,5-dihydroxy-2-[3(R)-(3-hydroxy-5-phenyl)pentyl]cyclopentyl}-5-heptenoate (Latanoprost, R23)

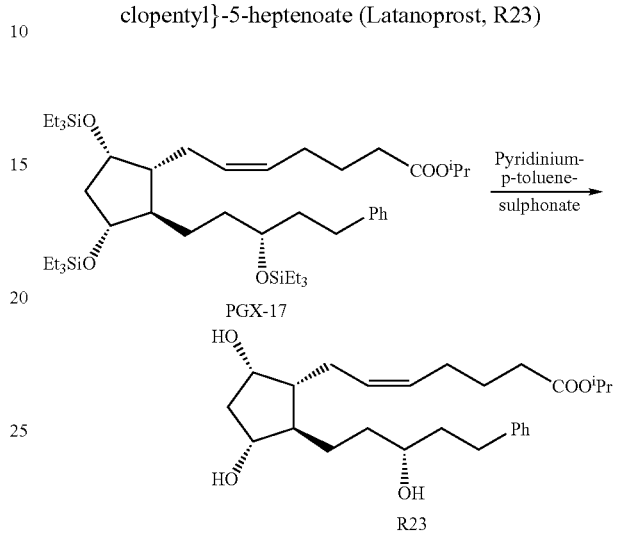

PGX-17 (170.0 g, 0.219M) was dissolved in acetone (1.9L) under an inert atmosphere and a solution of pyridinium-p-toluenesulphonate (4.52 g, 18.0 mMol, 0.08 eq.) in water (0.3L) added. The resulting mixture was stirred at ambient temperature for 3 h until TLC showed the reaction to be complete. After evaporation of the organic volatiles the residue was added to a mixture of ethyl acetate (2.1L) and brine (2L). The layers were separated and the aqueous phase further extracted with ethyl acetate (1L). The organics were combined and washed with brine (0.5L). Evaporation in vacuo gave a pale yellow oil (166.4 g). This was dissolved in hexane:ethyl acetate 1:1 (0.25L) and purified by chromatography on silica gel (1.87 Kg) eluting with hexane ethyl acetate (1:1 then 1:2 then 1:3). The relevant fractions were combined and evaporated to give an almost colourless oil (78.0 g). This was further purified by isocratic preparative HPLC on a silica column eluting with heptane (88-95%): methanol/isopropanol (1/2) (5-12%). Evaporation of the relevant combined cuts gave isopropyl (Z)-7-{(1R,2R,3R,5S)-3,5-dihydroxy-2-[3(R)-(3-hydroxy-5-phenyl)pentyl]cyclopentyl}-5-heptenoate (latanoprost) as an almost colourless oil (50.2 g, 53.0%).

Example 13b

HPLC Purification of Latanoprost

HPLC purification of latanoprost was carried out using a Waters$^{RTM}$ Spherisorb silica gel column. The isocratic eluent system comprised a hydrocarbon and an alcohol in volume percent ranges of 88-98% and 2-12% respectively. The hydrocarbons used were n-hexane, hexane fraction, n-heptane or heptane fraction. The alcohols used were isopropanol, ethanol or methanol, either singly or in combination in ratios of 1:1 to 3:1.

The results of typical HPLC runs using the above eluent system are shown below:

| Product | Amount | |
|---|---|---|
| | Run 1 | Run 2 |
| Latanoprost | 99.89% | 99.83% |
| 15(S)-cis isomer | 0.08% | 0.09% |
| 15(S)-trans isomer | 0.03% | 0.07% |
| 15(R)-trans isomer | not detected | not detected |

Thus, it can be seen that the above solvent system achieves a latanoprost purity of greater than 99.8% and the amounts of the undesired isomers are all less than 0.1%.

Example 13c

HPLC Separation of Latanoprost and Isomers

HPLC separations of latanoprost were carried out using a Waters$^{RTM}$ Spherisorb silica gel column. The isocratic eluent system comprised hydrocarbon:alcohol:acetonitrile in volume percent ratios of 90-96%:2-6%:24%. The hydrocarbons used were n-hexane, hexane fraction, n-heptane or heptane fraction. The alcohols used were either isopropanol or ethanol.

The following results are shown for a HPLC separation of latanoprost using as eluent, a mixture of heptane:isopropanol:acetonitrile in the volume percent ratios of 93%:4%:3%. The relative retention times of latanoprost, and the 15(S)-cis, 15(S)-trans and 15(R)-trans isomers are shown below:

| Product | Relative Retention Time |
|---|---|
| Latanoprost | 1.00 |
| 15(S)-cis isomer | 0.95 |
| 15(S)-trans isomer | 1.13 |
| 15(R)-trans isomer | 1.23 |

The above results indicate that an excellent degree of separation of latanoprost from the undesired isomers thereof can be achieved using an eluent system comprising acetonitrile. Similar results were achieved with Phenomenex$^{RTM}$Luna Cyano and Phenomenex$^{RTM}$Luna Silica columns. Using this procedure, it is possible to achieve latanoprost that is substantially pure, or is completely free, of the hitherto difficult to remove isomers.

The invention claimed is:

1. A process for the purification of latanoprost by HPLC comprising the use as an eluent, of a mixture comprising one or more hydrocarbons, one or more alcohols and acetonitrile.

2. A process according to claim 1 wherein the eluent comprises a hydrocarbon or a mixture of hydrocarbons in an amount range of 80-99 volume percent and an alcohol or a mixture of alcohols in an amount range of 1-20 volume percent.

3. A process according to claim 1 wherein the eluent comprises a hydrocarbon or a mixture of hydrocarbons in an amount range of 88-98 volume percent and an alcohol or a mixture of alcohols in an amount range of 2-12 volume percent.

4. A process according to claim 1 wherein the eluent comprises a hydrocarbon or a mixture of hydrocarbons in an amount range of 85-99 volume percent, an alcohol or a mixture of alcohols in an amount of 0.5-10 volume percent and acetonitrile in an amount of 0.5-5 volume percent.

5. A process according to claim 1 wherein the hydrocarbon is hexane or heptane.

6. A process according to claim 1 wherein the alcohol component comprises at least one $C_1$ to $C_8$ straight chain, branched or cyclic alkanol.

7. A process according to claim 1 wherein the alcohol comprises propan-2-ol.

8. Latanoprost free of the 15(S)-cis isomer, the 15(S)-trans isomer and the 15(R)-trans isomer.

9. Latanoprost containing less than 0.3% in total of any combination of: 15(S)-cis isomer, 15(S)-trans isomer and 15(R)-trans isomer.

10. Latanoprost according to claim 9 containing less than 0.1% each of 15(S)-cis isomer, 15(S)-trans isomer and 15(R)-trans isomer.

11. Latanoprost containing less than 0.3% in total of any combination of: the 15(S)-cis isomer, the 15(S)-trans isomer and the 15(R)-trans isomer, produced by a process comprising:
    (i) obtaining a mixture of isomers of latanoprost; and
    (ii) separating the latanoprost mixture by HPLC using as an eluent, a mixture comprising one or more hydrocarbons, one or more alcohols and, optionally, acetonitrile to yield latanoprost.

12. Latanoprost according to claim 11 having a purity of greater than 98%.

13. Latanoprost according to claim 12 having a purity of greater than 99%.

14. Latanoprost according to claim 12 having a purity of greater than 99.5%.

15. Latanoprost according to claim 12 having a purity of greater than 99.8%.

16. Latanoprost according to claim 11 wherein the eluent comprises at least one hydrocarbon, at least one alcohol and acetonitrile.

17. Latanoprost according to claim 11 wherein the eluent comprises a hydrocarbon or a mixture of hydrocarbons in an amount range of 80-99 volume percent and an alcohol or a mixture of alcohols in an amount range of 1-20 volume percent.

18. Latanoprost according to claim 11 wherein the eluent comprises a hydrocarbon or a mixture of hydrocarbons in an amount range of 88-98 volume percent and an alcohol or a mixture of alcohols in an amount range of 2-12 volume percent.

19. Latanoprost according to claim 11 wherein the eluent comprises a hydrocarbon or a mixture of hydrocarbons in an amount range of 85-99 volume percent, an alcohol or a mixture of alcohols in an amount of 0.5-10 volume percent and acetonitrile in an amount of 0.5-5 volume percent.

20. Latanoprost according to claim 11 wherein the hydrocarbon is hexane or heptane.

21. Latanoprost according to claim 11 wherein the alcohol component comprises at least one $C_1$ to $C_8$ straight chain, branched or cyclic alkanol.

22. Latanoprost according to claim 11 wherein the alcohol comprises propan-2-ol.

* * * * *